(12) United States Patent
Kamihara et al.

(10) Patent No.: US 9,488,667 B2
(45) Date of Patent: Nov. 8, 2016

(54) AUTOMATIC ANALYZER

(75) Inventors: Kumiko Kamihara, Mito (JP); Satoshi Mitsuyama, Tokyo (JP); Tomonori Mimura, Kasama (JP); Chihiro Manri, Kawagoe (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1004 days.

(21) Appl. No.: 13/318,819

(22) PCT Filed: Apr. 12, 2010

(86) PCT No.: PCT/JP2010/002632
§ 371 (c)(1),
(2), (4) Date: Nov. 30, 2011

(87) PCT Pub. No.: WO2010/131413
PCT Pub. Date: Nov. 18, 2010

(65) Prior Publication Data
US 2012/0065898 A1  Mar. 15, 2012

(30) Foreign Application Priority Data

May 11, 2009 (JP) ................................. 2009-114112

(51) Int. Cl.
*G01C 19/00* (2013.01)
*G01N 35/00* (2006.01)

(52) U.S. Cl.
CPC . *G01N 35/00613* (2013.01); *G01N 2035/0097* (2013.01)

(58) Field of Classification Search
CPC .............. G01N 35/00613; G01N 2035/0097
USPC .................................................. 702/104, 19
See application file for complete search history.

(56) References Cited

U.S. PATENT DOCUMENTS

| 2006/0089810 A1* | 4/2006 | Matsumoto et al. ........... 702/19 |
| 2007/0178504 A1* | 8/2007 | Colpitts et al. .................. 435/6 |
| 2008/0133141 A1* | 6/2008 | Frost ............................... 702/19 |

(Continued)

FOREIGN PATENT DOCUMENTS

| EP | 0 272 407 A2 | 6/1988 |
| JP | 57-147039 A | 9/1982 |

(Continued)

OTHER PUBLICATIONS

Thompson, "Development of an automated photometric assay for serum lithium and use of binding equilibrium expressions to optimize results", 2003, Clinica Chimica Acta, 149-156.*

*Primary Examiner* — Mischita Henson
*Assistant Examiner* — Stephanie Bloss
(74) *Attorney, Agent, or Firm* — Mattingly & Malur, PC

(57) ABSTRACT

To change a photometric time for each item or to change a measurement time for each specimen so that time required for biochemical measurement can be reduced, an index that indicates an end of a reaction is required. Unfortunately, however, no methods have been available for determining the end of the reaction. In measuring a substance to be measured contained in a sample, a parameter in an approximate expression is calculated using a measured value that changes with time, a degree of convergence of a reaction is determined according to a degree of convergence of the parameter, and a measured value at the end of the reaction is calculated using the parameter at a point in time at which it is determined that the reaction has converged.

22 Claims, 15 Drawing Sheets

(56) References Cited

U.S. PATENT DOCUMENTS

| | | | |
|---|---|---|---|
| 2009/0040517 A1* | 2/2009 | Maier et al. | 356/301 |
| 2010/0099194 A1* | 4/2010 | Okabayashi | 436/55 |

FOREIGN PATENT DOCUMENTS

| | | | | |
|---|---|---|---|---|
| JP | 63-111446 A | 5/1988 | | |
| JP | 64-59041 A | 3/1989 | | |
| JP | 3-59461 A | 3/1991 | | |
| JP | 4-50752 | 2/1992 | | |
| JP | 6-194313 | * 7/1994 | G01N 21/75 |
| JP | 6-194313 A | 7/1994 | | |
| JP | 6-0249856 | * 9/1994 | | |
| JP | 6-249856 A | 9/1994 | | |
| JP | 8-219984 A | 8/1996 | | |
| JP | 2006-337125 A | 12/2006 | | |

* cited by examiner

FIG. 11

| TEST ITEMS | REAGENT | APPROXIMATE EXPRESSION | REACTION TIME |
|---|---|---|---|
| ITEM A | REAGENT A | EXPRESSION 1 | 4 |
| ITEM A | REAGENT B | EXPRESSION 2 | 3 |
| ITEM B | REAGENT C | EXPRESSION 7 | 5 |
| ITEM B | REAGENT D | EXPRESSION 9 | 4 |
| ⋮ | ⋮ | ⋮ | ⋮ |

AUTOMATIC ANALYZER

TECHNICAL FIELD

The present invention relates to automatic analyzers that perform a qualitative/quantitative analysis of a biological sample such as blood and urine in terms of a plurality of items. The invention more particularly relates to an automatic analyzer that includes a function for monitoring and measuring changes with time in a degree of a plurality of components contained in a biological sample affecting measurement of an intended substance to be measured.

BACKGROUND ART

An automatic analyzer for clinical tests dispenses predetermined amounts of a reagent and a sample for subsequent mixing and reaction. Absorbance of a reaction solution is then measured for a predetermined period of time and, based on measurements, concentration of substances to be measured are found.

The number of tests per hour is used as an index indicating processing capacity of apparatuses. Since the development of the automatic analyzers, a number of manufacturers of automatic analyzers have been making effort to develop means of increasing the processing speed of the apparatuses, in addition to enhanced accuracy of measurements. Efforts toward the increased processing speed of the apparatuses have been embodied in such areas as the increased number of reaction cells to be used (increased size of the apparatus), higher dispensing speed of probes for specimens and reagents (higher probe motions), faster and more efficient specimen rack transfer lines, and higher data processing speed of PCs. This has resulted in a substantially shorter time between blood sampling to measurements report. One of factors that limit the processing speed of measurement in current automatic analyzers that offer a higher throughput is time it takes a specimen and a reagent to react with each other, a reaction time, during measurement. The reaction time depends on reactivity of the reagent. The reaction time in biochemical analyzers is typically ten minutes per one item. Sample-and-reagent reaction end time varies greatly for each item and measurement methods of clinical tests can be classified into an endpoint assay and a rate assay according to the analysis method.

In the endpoint assay, a change in absorbance decreases with time and eventually approaches asymptotically a predetermined value (final absorbance). Concentration of the component to be measured in the sample is obtained from the value of absorbance which the change in absorbance asymptotically approaches. Even with the endpoint assay, the final absorbance is reached at relatively early stages with some items, such as T-CHO (total cholesterol) and Glu (glucose). While, with other items, such as CRE (creatinine), TP (total protein), CRP (C-reactive protein) by an immuno-turbidimetric method, IgA (immunoglobulin A), IgG (immunoglobulin G), and IgM (immunoglobulin M), with which a reaction progresses only mildly and takes time to reach the final absorbance by way of a final steady state.

The rate assay is typically a test method that measures a speed at which a reaction progresses from a start of the reaction between a specimen and a reagent. A rate of change in absorbance of the rate assay substantially remains constant and the reaction process is linear. With an enzyme method as a type of the rate assay, the reaction continues until a substrate or a coenzyme is consumed, so that the absorbance continues increasing or decreasing and is not constant, except when the specimen concentration is so high as to exceed a permissible range. An activity value of the item is therefore calculated from the speed of the linear change in absorbance, and not the concentration of the enzyme itself. If the reaction stops within a measurement time for use in speed calculation and the absorbance undergoes a sudden change, and if the absorbance at that particular point is used, concentration of the item cannot be measured correctly. The reaction speed is therefore calculated without using the absorbance at that photometric point. In patent document 1, a calculation method that eliminates the need for dilution and repeat run may be employed.

As a method for obtaining favorable measurements even when a sufficiently long time cannot be made available for the reaction time, patent document 2, for example, discloses a method for approximating a relationship between absorbance and time with $y=A+(B-A)/\exp(Kt)$, using measured time and absorbance data and the least squares method. Where, A denotes final absorbance, B denotes reaction initial absorbance, K denotes a reaction speed constant, and t denotes measurement time. In this method, the concentration of the substance to be measured is obtained based on obtained A, B, and K.

PRIOR ART DOCUMENTS

Patent Documents

Patent Document 1
JP-1-59041-A
Patent Document 2
JP-6-194313-A

SUMMARY OF THE INVENTION

Problem to be Solved by the Invention

The clinical test field in hospitals requires that measurements of patient specimens be reported as soon as possible. Obtaining measurements rapidly is essential in facilities required to take immediate action, such as, nighttime emergency medical care and sites where a disaster occurs or medical treatment is being provided, in particular. Lately, some hospitals perform pre-examination tests of specimens for ordinary patients and provide, during physical examination, medical treatment based on the measurements taken earlier. Test measurements are known at the first medical examination, so that the patient can be relieved of a burden of revisiting the hospital for results. Needless to say, the shorter the time it takes from blood drawing to report of measurements, the better both for the patient and the side providing medical treatment. Time it takes from blood drawing to measurement report in clinical tests may be analyzed and classified into the following three categories: 1) time during which a blood specimen drawn from the patient is left to stand before centrifugal separation; 2) time during which the specimen is set in an analyzer and undergoes measurement; 3) time during which the specimen undergoes transfer from one place to another and centrifugal separation, patient information is registered, measurements are reported, and related processing is performed. Time of specimen transfer and data processing in category 3) has been reduced considerably thanks to, for example, systematization of specimen transfer systems and entire test chamber systems. Time of category 1) to leave the specimen to stand has also been considerably reduced thanks to development and spread of the high-speed coagulation type blood collection tube. No change of ten minutes in the reaction time of automatic analyzers of category 2) has, however, been made in the past 30 years. A system is incorporated in which ordinary specimens that flow routinely are interrupted by an urgent specimen in, for example, current biochemical automatic analyzers for preferential measurement. Time of reaction between the specimen and the reagent for the urgent specimen is, however, the same as that for the ordinary specimen. At least a predetermined period of time of about ten minutes is required before measurements are given after the specimen is set. Even with a processing speed of the specimen transfer system or dispensing speed by the probe on the apparatus side made faster, therefore, there arises another need for a shorter reaction time in order to achieve even faster measurement. Simply shortening the measurement time, however, results in absorbance at a point in time at which the reaction is incomplete, so that measurements of concentration and an activity value derived from such absorbance are only inaccurate.

Reagents for measuring components in biological samples are used in, for example, enzyme reaction, antigen-antibody reaction, chelate reaction, and electrode method. In the electrode method for measuring ions, such as K (kalium) and Na (natrium), in the sample, it takes as short a time as about one minute to complete the measurement. The chelate reaction used for measuring inorganic substances, such as Mg (magnesium) and Fe (iron) takes as short as less than 1 minute for the sample-and-reagent reaction time. The reaction time of enzyme reaction, on the other hand, depends on the speed of reaction between the enzyme and substrate. Substrate concentration, temperature, pH, and other factors affect, so that a reaction time of more than two minutes is required in longer reaction. In the antigen-antibody reaction, a reaction constant of the antigen and the antibody is small, so that the reaction is not generally completed after five minutes of an application of the antibody. Specifically, the reaction time of the enzyme reaction and the antigen-antibody reaction is determined by a reaction speed constant of the enzyme itself. Time of reaction between the specimen and the reagent varies greatly depending on the item or specimen concentration in this manner and some items may actually require less than ten minutes for reaction. However, to have a specific photometric time for each item or a specific measurement time for each specimen, an index is necessary that indicates that the reaction is completed. Reaction process data does serve that purpose, but no methods have been available for determining that the reaction is completed.

Patent document 1 describes that the concentration of the substance to be measured can be accurately obtained even if a long reaction time cannot be made available. Even if the method disclosed in this document is used, an error in concentration of the substance to be measured obtained finally is smaller at longer reaction times, considering errors contained in measured data. There is, however, a problem in that a reaction time to be specifically set is unknown. Another problem is that it is difficult to find an optimum reaction time, since the optimum reaction time varies according to the type of the substance to be measured or the type of reagent used.

Means for Solving the Problem

An arrangement of the present invention for solving the above-described problems is as described below.

An automatic analyzer includes: a storage mechanism for storing approximate expressions for a change in a measured value with time, each of the approximate expressions being associated with a corresponding test item or specimen; a parameter optimizing mechanism for optimizing a parameter of the approximate expressions whenever a value is measured at predetermined intervals; and a determining mechanism for determining whether a change in the parameter optimized by the parameter optimizing mechanism falls within a predetermined range.

The storage mechanism stores information and may be any mechanism as long as the mechanism can store information. Examples include, but are not limited to, a semiconductor memory, a hard disk storage device, a floppy (a registered trademark) disk storage device, and an optical magnetic storage device. The storage mechanism is typically disposed inside a cabinet of a control computer, but may be an independent mechanism. The parameter optimizing mechanism determines each of multiple parameters of an approximate expression using a parameter fitting algorithm, such as the least squares method, so that the parameter best fits actual data. The parameter optimizing mechanism is typically formed of software built into a control computer or a dedicated computer and hardware for operating the software. The parameter optimizing mechanism may nonetheless be a mechanism of any mode, as long as the mechanism can determine parameters through parameter fitting.

The determining mechanism interprets as a parameter change (variation) the way in which the parameter calculated by the parameter optimizing mechanism approaches asymptotically a predetermined value and determines whether the change falls within a predetermined range, specifically, whether the parameter determined by the parameter optimizing mechanism falls within a predetermined range, through a comparison with an upper limit value or a lower limit value, a comparison of an absolute value of the variation with a threshold value, or a multivariate analysis, for example, such techniques as the Mahalanobis-Taguchi method and a neural network. The determining mechanism is typically formed of software built into a control computer or a dedicated computer and hardware for operating the software. The determining mechanism may nonetheless be a mechanism of any mode, as long as the mechanism can determine a degree of changes in the parameter.

A preferred embodiment of the present invention will be described below.

The present invention focuses on reaction process data that serves as footprints of a reaction from beginning to end between a sample and a reagent in an automatic analyzer and finds an approximate expression of the reaction process sequentially each time measurement data, such as absorbance, of the substance to be measured is obtained during measurement. By calculating concentration of the substance to be measured at a predetermined point in time using a parameter value of the approximate expression obtained, concentration of the substance to be measured contained in the sample is estimated.

The above problem can be solved by obtaining an approximate expression using measured values that change with time during measurement of the substance to be measured contained in the sample and calculating concentration of the substance to be measured at a predetermined point in time from the approximate expression obtained. In FIG. 3, an abscissa 110 represents time elapsed, while an ordinate 120 represents the absorbance. A broken line 130 represents a point in time at which a second reagent is applied. A symbol 140 represents an absorbance value actually measured and a curve 150 represents changes with time in the absorbance obtained with the approximate expression. Then, a measured value can be obtained with a photometric time at a point used for approximation without having to wait for an actual reaction time of ten minutes. Such a use eliminates the need for observing the absorbance until the reaction is completed, allowing a measured value to be calculated before the reaction is completed.

Preferably, the embodiment includes means for comparing measurement data described by the approximate expression with time-series data stored sequentially. This allows an optimum reaction time to be identified.

Additionally, from the approximate expression, a value of a parameter reflecting a status of the measured value that changes with time is calculated and the calculated value of the parameter is sequentially stored. When a value of a parameter previously stored and a value of a parameter newly stored are stable, concentration of a substance to be measured at a predetermined point in time is calculated. This allows the concentration to be calculated for an optimum reaction time.

Additionally, from the approximate expression, a value of a parameter reflecting the status of the measured value that changes with time is calculated and concentration of a substance to be measured is calculated from the value of the parameter. The calculated concentration of the substance to be measured is then stored. When a value of the concentration of the substance to be measured previously stored and a value of the concentration of the substance to be measured newly stored are stable, the concentration of the substance to be measured is output. This allows the concentration to be output for an optimum reaction time.

Additionally, from the approximate expression, a value of a parameter reflecting the status of the measured value that changes with time is calculated and a measured value of a substance to be measured is estimated from the value of the parameter. Concentration of the substance to be measured is calculated at a point in time at which deviation from an actually measured value is small is calculated, thereby allowing the concentration to be calculated for an optimum reaction time.

A plurality of types of expressions containing one or more parameters that reflect the status of the measured value that changes with time is stored and one type of expression is selected from among the multiple expressions according to the type of the substance to be measured or the type of reagent to be used. An optimum type of expression to be used may be determined in advance through a verification experiment for each type of reagent or item. Alternatively, calculations are performed using the multiple types of expressions and the approximate expression that yields a small residual error from reaction process data obtained as time elapses (a difference between absorbance obtained through actual measurement and absorbance calculated using the approximate expression) is adopted as the final approximate expression for concentration estimation. Calculating the approximate expression allows the change in absorbance with time to be more accurately approximated than the related art, permitting even easier setting of an optimum reaction time.

Effects of the Invention

If the reaction curve can be accurately identified through the use of the present invention, measurements can be taken without having to go through the existing reaction time of ten minutes. This allows measurements of the urgent specimen to be obtained rapidly. A shorter measurement time can be achieved for not only the urgent specimen, but also ordinary specimens. The automatic analyzer according to the present invention calculates reaction using several points immediately following the start of reaction of a plurality of points in a total reaction time. Concentration is calculated from the absorbance after the reaction. Since there is no need to follow through all reaction time, the measurement time of the specimen can be considerably shortened and efficiency in biochemical measurement through the use of the automatic analyzer can be expected to be enhanced.

In addition, if there is deviation between a value calculated in the beginning of reaction and a value calculated at the end of the reaction, a data alarm indicating an abnormal reaction can be issued, which enhances data reliability.

BRIEF DESCRIPTION OF THE DRAWINGS

FIG. 11 is an example of a table describing optimum approximate expressions and reaction times relative to different combinations of a test time and a reagent used.

MODES FOR CARRYING OUT THE INVENTION

Embodiments of the present invention will be described below with reference to the accompanying drawings.

First Embodiment

Figure 2:
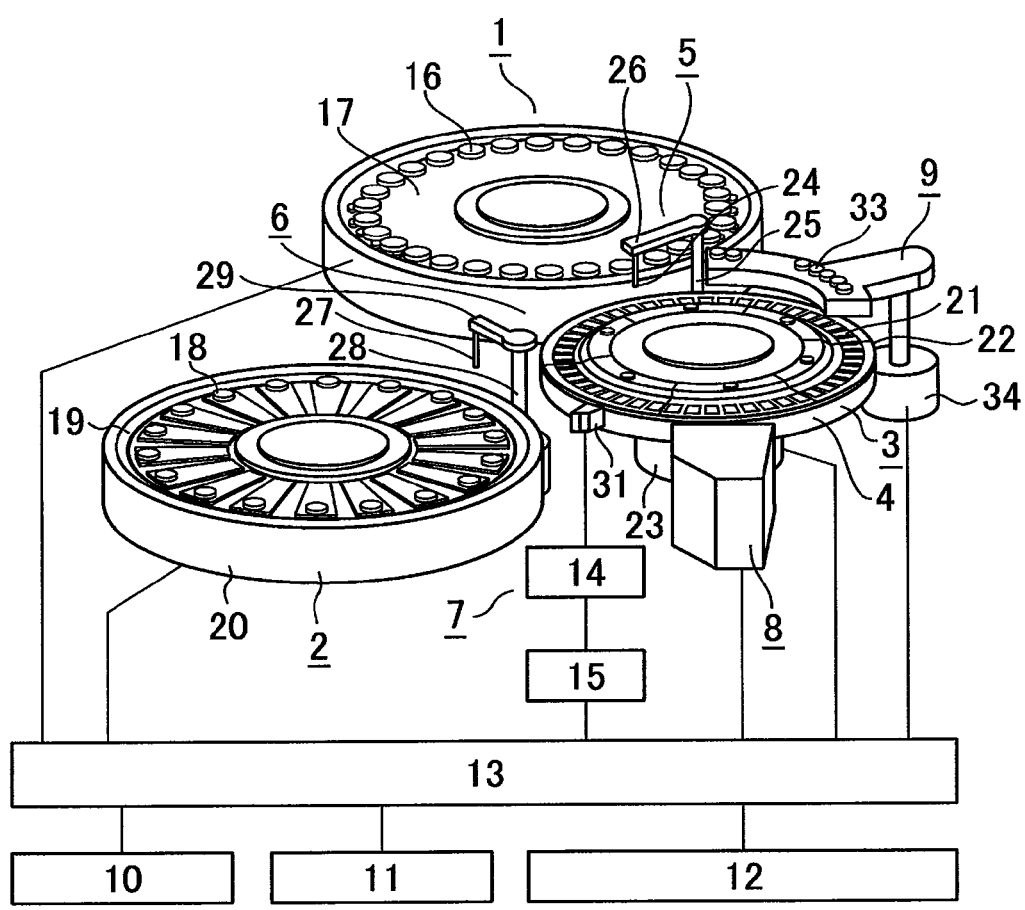
FIG. 2 is a flow chart showing processes performed according to a first embodiment of the present invention.

An automatic analyzer according to a first embodiment of the present invention will be described in detail below. FIG. 2 is an illustration showing schematically arrangements of a biochemical automatic analyzer to which the present invention is applied, wherein reference numeral 1 denotes a sample disk, reference numeral 2 denotes a reagent disk, reference numeral 3 denotes a reaction disk, reference numeral 4 denotes a reaction tank, reference numeral 5 denotes a sampling mechanism, reference numeral 6 denotes a pipetting mechanism, reference numeral 7 denotes a mixing mechanism, reference numeral 8 denotes a photometry mechanism, reference numeral 9 denotes a rinsing mechanism, reference numeral 10 denotes a display section, reference numeral 11 denotes an input section, reference numeral 12 denotes a storage section, reference numeral 13 denotes a control section, reference numeral 14 denotes a piezoelectric element driver, reference numeral 15 denotes a mixing mechanism controller, reference numeral 16 denotes a sample vessel, reference numerals 17, 19 denote circular disks, reference numeral 18 denotes a reagent bottle, reference numeral 20 denotes a cool box, reference numeral 21 denotes a reaction vessel, reference numeral 22 denotes a reaction vessel holder, reference numeral 23 denotes a drive mechanism, reference numerals 24, 27 denote probes, reference numerals 25, 28 denote bearing shafts, reference numerals 26, 29 denote arms, reference numeral 31 denotes a fixing section, reference numeral 33 denotes a nozzle, and reference numeral 34 denotes a vertical drive mechanism. The storage section stores, for example, analysis parameters, number of analyses to be made by each reagent bottle, maximum number of analyses to be made, calibration results, and analyses. The sample is analyzed in the following sequence as detailed below: sampling, dispensing reagent, mixing, photometric measurement, rinsing reaction vessel, and converting concentration and other data processing operations.

The control section 13 controls the sample disk 1 via the display section 10. A plurality of sample vessels 16 are arranged in a circle on the sample disk 1, being moved to a position beneath the sampling probe 24 according to an order of samples to be analyzed. A predetermined amount of specimen in the specific sample vessel 16 is dispensed into the reaction vessel 21 by a sample pump connected to the specimen sampling mechanism 5.

The reaction vessel 21 into which the sample is dispensed moves to a first reagent adding position in the reaction tank 4. A predetermined amount of reagent picked up from the reagent vessel 18 is added to the moved reaction vessel 16 by a reagent pump (not shown) connected to the reagent dispensing probe 6. The reaction vessel 21 into which the first reagent is added moves to a position of the mixing mechanism 7, at which first mixing is performed. Such operations of adding and mixing the reagent are performed for each of first to fourth reagents.

The reaction vessel 21 in which contents are mixed passes through a flux of light emitted from a light source, so that the photometry mechanism 8 of a multiwavelength photometer detects absorbance prevailing at that time. A signal representing the detected absorbance enters the control section 13 and is converted to corresponding concentration of the specimen.

The data obtained through conversion to concentration is stored in the storage section 12 and displayed on the display section. The reaction vessel 21 that has undergone the photometric measurement is moved to the rinsing mechanism 9, rinsed, and served for a subsequent analysis.

Figure 1:
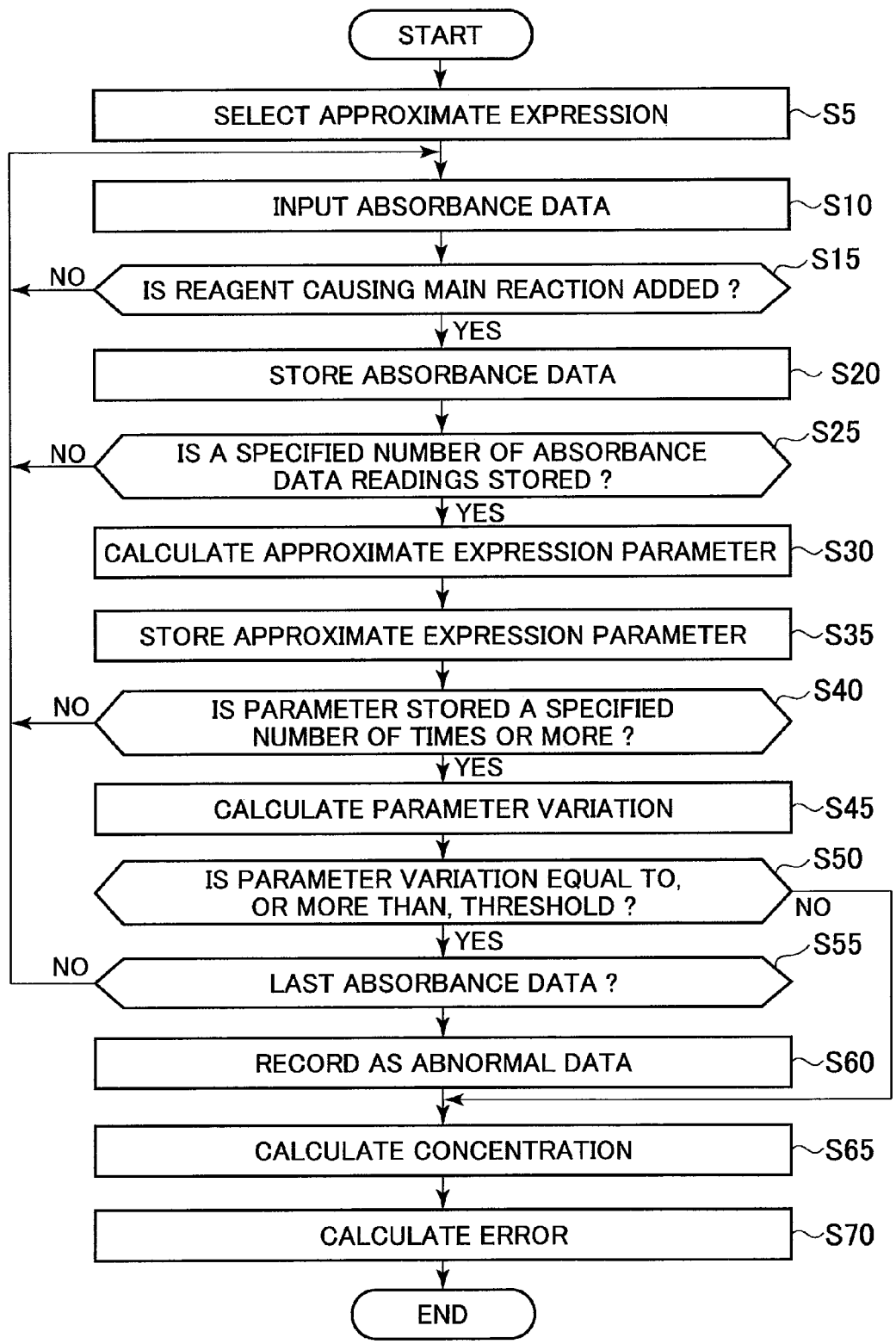
FIG. 1 is an illustration showing schematically arrangements of an automatic analyzer to which the present invention is applied.

Processes for conversion to corresponding concentration of the specimen in the control section 13 will be described in detail below with reference to FIG. 1. FIG. 1 is a flow chart showing processes performed by portions involved in conversion to concentration in the control section 13. At the same time that measurement of a test item is started for a specimen, an approximate expression associated with the test item is selected in step S5 from among a plurality of approximate expressions representing changes in absorbance with time.

Figure 3:
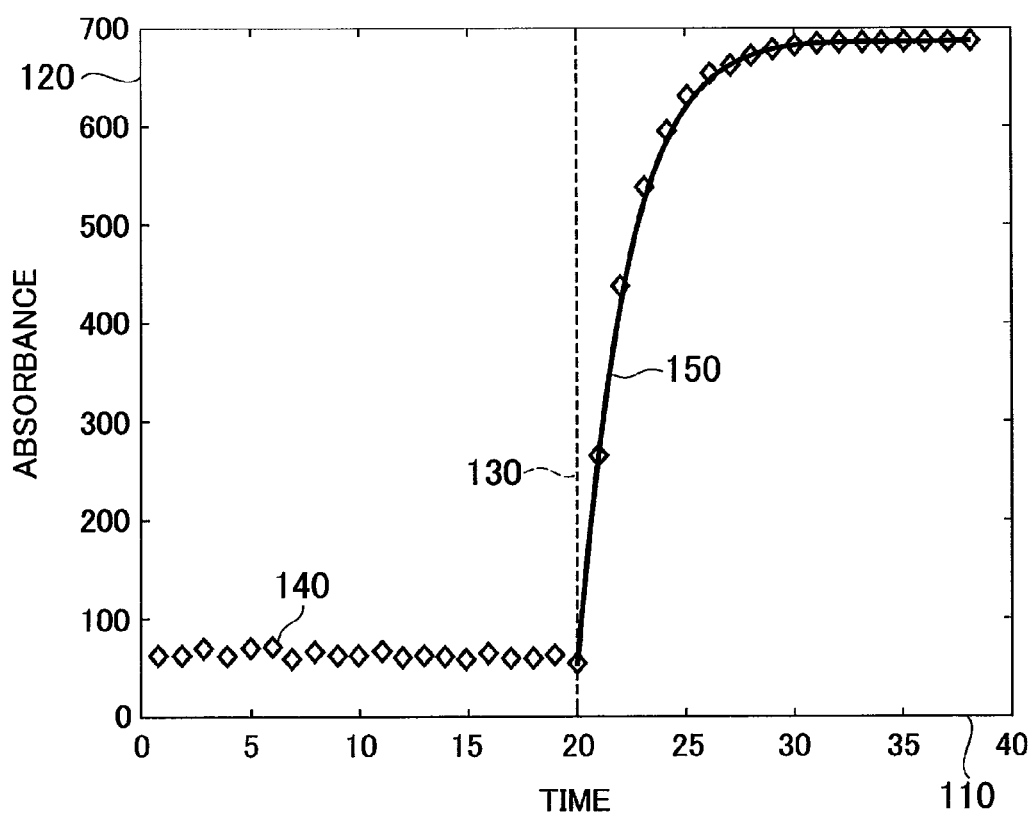
FIG. 3 is a graph showing changes with time in absorbance in measurement taken according to an endpoint assay.
Figure 4:
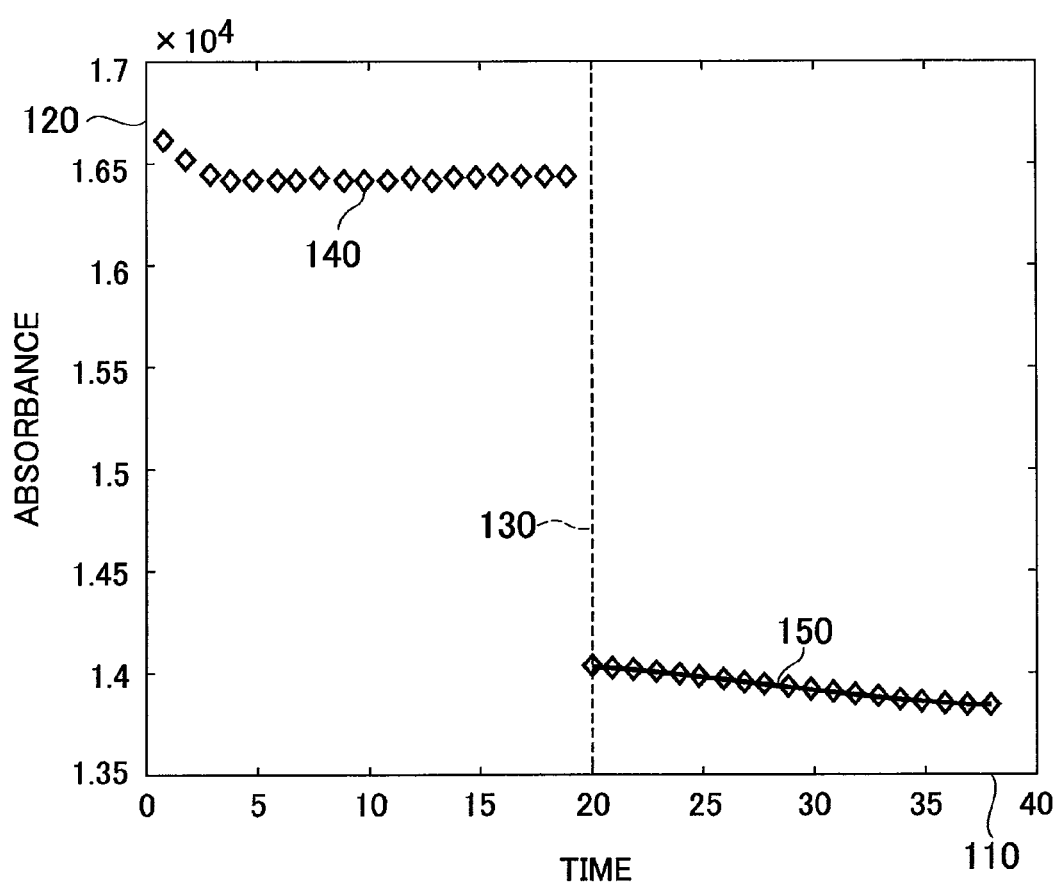
FIG. 4 is a graph showing changes with time in absorbance in measurement taken according to a rate assay.

As mentioned in Background Art, the measurement method may be classified broadly into two types: the endpoint assay and the rate assay. Changes in absorbance vary greatly between these two types. FIGS. 3 and 4 show typical changes with time in absorbance in the endpoint assay and the rate assay. Referring to FIGS. 3 and 4, an abscissa 110 represents time, while an ordinate 120 represents the absorbance. The reaction involved is a two-reagent reaction, in which changes in absorbance for measuring the substance to be measured start after a second reagent is applied. In FIGS. 3 and 4, a broken line 130 represents a specific point in time at which the second reagent is applied. A symbol 140 represents an absorbance value actually measured and a curve 150 represents the change in absorbance with time obtained by an approximate expression.

In the endpoint assay, the absorbance approaches asymptotically a predetermined value as the reaction progresses as shown in FIG. 3. In the rate assay, on the other hand, the absorbance changes substantially linearly as shown in FIG. 4. This requires that each of these two methods use a unique approximate expression that is different from each other. Further, even the same endpoint assay or the same rate assay exhibits a slightly different change with time depending on the item. A plurality of expressions is therefore made available and an optimum approximate expression is selected according to the item.

For example, the following expressions to be used in the endpoint assay are made available to choose from. Where, x denotes absorbance, t denotes time, and a0, a1, a2, b0, b1, c, d, e, r, s, k1, and k2 denote parameters.

$$x = a0 + a1 * \exp(-k1 * t) \qquad \text{(Expression 1)}$$

$$x = a0 + a1 * \exp(-k1 * t) + a2 * \exp(-k2 * t) \qquad \text{(Expression 2)}$$

$$x = c + (1/(b0 + b1 * t)) \qquad \text{(Expression 3)}$$

$$x = d + (e/(\exp(r * t) + s)) \qquad \text{(Expression 4)}$$

(Expression 1) and (expression 2) are generalized to obtain an expression given below, where n denotes a natural number and $\Sigma\{\ \}$ denotes a symbol representing a sum of all values, each value being obtained by substituting i in $\{\ \}$ for a value of 1 to n. (Expression 5) may also be used with n being a variety of natural numbers.

$$x = a0 + \Sigma\{ai * \exp(-ki * t)\} \qquad \text{(Expression 5)}$$

An expression of the following format can be used for the rate assay, where x denotes absorbance, t denotes time, and a and b denote parameters. $h(t, \psi)$ contains a plurality of parameters $\psi$ and denotes a function that approaches asymptotically zero with t being infinity.

$$x = a * t + b + h(t, \psi) \qquad \text{(Expression 6)}$$

With the rate assay, the absorbance changes linearly with time, so that the absorbance x is ideally a linear expression of t, x=a*t+b. In actual reaction, however, the reaction speed is not constant in the beginning of the reaction and the reaction process may change in a curve (a lag time). $h(t, \psi)$ in the above expression is a term for accurately approximating the curved portion in the beginning of the reaction. Expressions given below may, for example, be used, in which $h(t, \psi)$ is embodied. Where, x denotes absorbance, t denotes time, and a, b, c1, d, e, k1, ci, ki, u, v, w, p, q, and r denote parameters. In addition, n denotes any natural number and $\Sigma\{\ \}$ denotes a symbol representing a sum of all values, each value being obtained by substituting i in $\{\ \}$ for a value of 1 to n.

$$x = a^*t + b + c1^*\exp(-k1^*t) \quad \text{(Expression 7)}$$

$$x = a^*t + b + \Sigma\{ci^*\exp(-ki^*t)\} \quad \text{(Expression 8)}$$

$$x = a^*t + b + e/(t+d) \quad \text{(Expression 9)}$$

$$x = a^*t + b + w/\{\exp(u^*t) + v\} \quad \text{(Expression 10)}$$

$$x = a^*t + b + p^*\log\{1 + q^*\exp(r^*t)\} \quad \text{(Expression 11)}$$

(Expression 6) to (expression 11) approximate changes in absorbance, in which the absorbance changes with time in a curve in the beginning of the reaction and then linearly. Depending on the test item, however, the change may again be in a curve at the end of the reaction. In such cases, expressions for approximating general curves, such as higher-order polynomials, may be used. Such expressions for approximating general curves will be expressed by a format shown in (expression 12) given below. Where, t denotes time, x denotes absorbance, and $\phi$ denotes a plurality of parameters.

$$x = g(t, \phi) \quad \text{(Expression 12)}$$

The absorbance is measured a plurality of times as time elapses. In step S10, absorbance data of a value measured once is input from the photometry mechanism 8. In a measuring system that uses light with two wavelengths, one with a wavelength (main wavelength) with which the absorbance varies greatly according to a change in tone involved in reaction between the reagent and the specimen and the other with a wavelength (sub-wavelength) with which the absorbance changes little, a difference between absorbance of the main wavelength light and absorbance of the sub-wavelength light is input as the absorbance data.

Referring to FIGS. 3 and 4, in a reaction in which a plurality of reagents is used, a large change in absorbance begins after a reagent (typically, a final reagent) causing a major change in absorbance is applied. In step S15, it is therefore determined whether the reagent causing a major change in absorbance is applied. If it is determined that such a reagent is yet to be applied, control is returned back to S10 and the next absorbance data is input. If it is determined that such a reagent has been applied, control is passed onto step S20, in which the input absorbance data is stored.

In step S25, it is determined whether a number of absorbance data readings is stored required for calculating a value of a parameter in an expression that describes changes with time in absorbance and an expression that yields as small an actual change with time in absorbance as possible. Generally, in order to calculate the value of a parameter in the expression, the data readings equal in number to that of the parameters are required. If it is determined in step S25 that the required number of data readings are yet to be stored, the control is returned to step S10 and the next absorbance data is input. If it is determined that the required number of data readings are stored, the control is passed onto step S30.

In step S30, the value of the parameter is calculated in an expression that describes changes with time in absorbance and an expression that yields as small an actual change with time in absorbance as possible and the calculated parameter value is stored in step S35. Specifically, in step S30, the parameter value in the expression is established so that a square error between the measured and stored absorbance data and the absorbance, calculated using (expression 1) to (expression 12), at the same point in time as that at which the absorbance is measured is as small as feasible. A known least squares calculation method may be employed for calculating the parameter value. A method that may be applied to expressions of various formats, for example, the steepest descent method, may be employed to calculate the parameter value that results in the square error being the smallest.

In step S40, it is determined whether the parameter is stored a number of times required for calculating the concentration. In subsequent calculations, the concentration value is calculated from the parameter. Generally speaking, however, the smaller the number of data readings observed, the greater the number of errors included in the calculated concentration value. In this embodiment, therefore, in order to prevent a concentration value containing a large number of errors from being output, a minimum number of calculations to be performed to calculate the parameter, required for calculating the concentration is set. In step S40, it is determined whether the parameter is calculated the set number of times or more. If it is determined that the parameter is not calculated the set number of times, the control is returned back to step S10 and the next absorbance data is input. If it is determined that the parameter is calculated the set number of times or more, the control is passed onto step S45.

Figure 5:
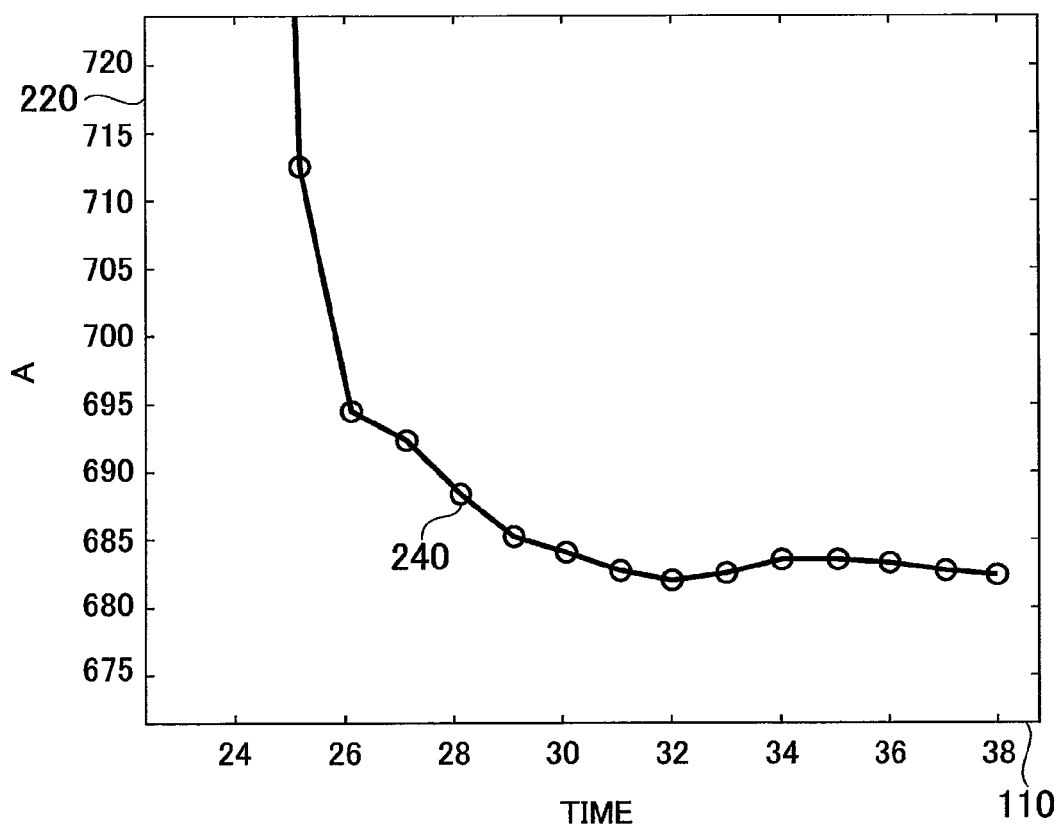
FIG. 5 is a graph showing changes in calculated parameter values.

In step S45, a magnitude of a variation with time in the calculated parameter is calculated. In the present invention, processes are repeated in which the absorbance is measured after the reaction is started and the expression parameter is obtained. The calculation of the expression parameter is to estimate the expression parameter such that the parameter matches with the observed absorbance as much as possible. In the beginning of the reaction during which the number of absorbance data readings available remains small, however, the error contained in the data contributes to a greater error contained in the estimated parameter. As the number of absorbance data readings increases with time, random errors contained in the absorbance data are offset, resulting in a smaller error contained in the estimated parameter. As a result, in the beginning of the reaction, the value of the parameter estimated each time is varied as affected by the error contained in the absorbance. As the number of data readings increases, however, the variation in the parameter becomes small and the parameter converges to an optimum value. FIG. 5 is a graph in which a parameter value at each point in time at which the absorbance is observed is obtained from actual absorbance data and these parameter values are plotted. An abscissa 110 represents time, while an ordinate 220 represents parameter values. A symbol 240 represents a parameter value calculated at each point in time.

Figure 6:
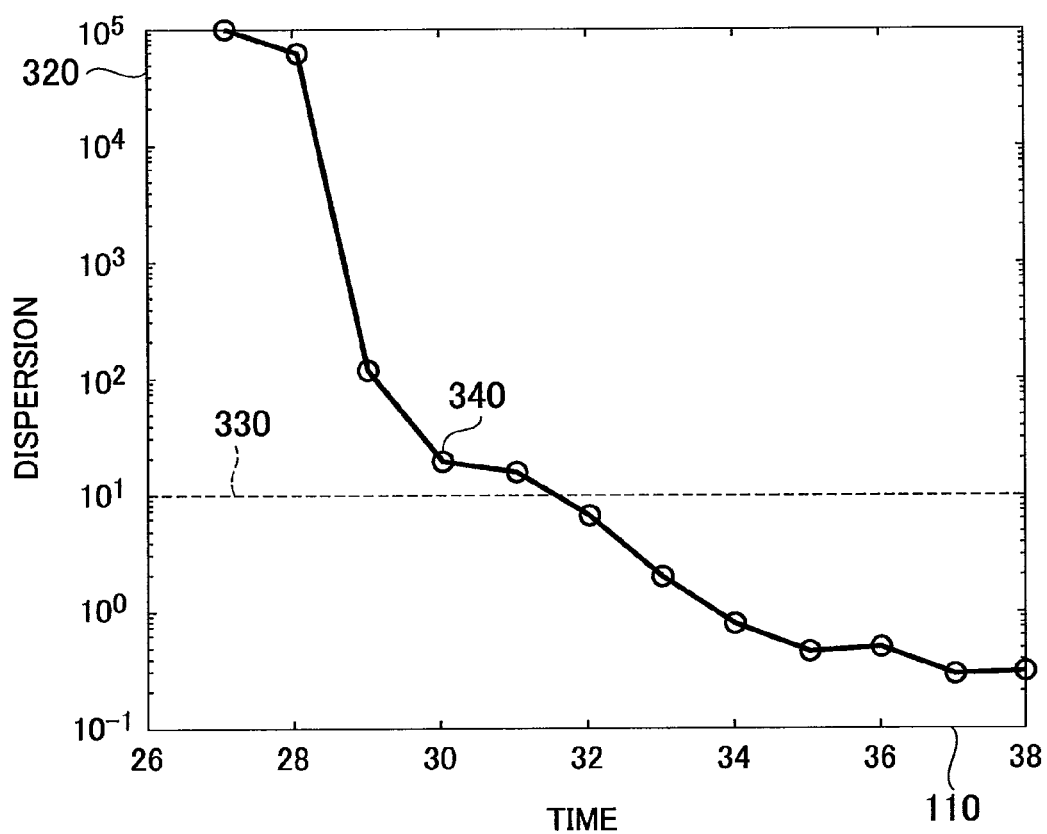
FIG. 6 is a graph showing changes in dispersion of calculated parameter values.

In step S45, the variation with time in the parameter is digitized. Various methods can be used for digitizing the variation in the parameter. For example, a difference from a parameter value calculated immediately before a current one, dispersion of parameter value variations for past several ones immediately before the current one, or a difference between a maximum value and a minimum value of several parameter value variations may be used. FIG. 6 is a graph showing dispersion values plotted as the variation with time in the parameter, each dispersion value being a total of five parameter value variations of a current one at a specific point in time and four preceding ones before the current one. An abscissa 110 represents time elapsed, while an ordinate 320 represents dispersion of parameter values. A symbol 340 represents a dispersion value calculated at each point in time.

In step S50, the variation with time in the parameter obtained in step S40 is compared with a predetermined threshold value. If the variation in the parameter is equal to, or less than, the predetermined threshold value, it is then determined that a sufficient amount of absorbance data required for calculating the concentration of the substance to be measured has been stored, so that the control is passed onto step S65 in which the concentration is calculated. If the variation in the parameter is greater than the predetermined threshold value, it can then be considered that the sufficient amount of absorbance data required for calculating the concentration of the substance to be measured is yet to be stored. The control is then passed onto step S55 in which it is determined whether another data reading is available. The threshold value for comparison of the variation in the parameter is set in advance so as to achieve required measurement accuracy according to the purpose of the apparatus. It is noted that an arrangement may be made so as to allow the threshold value to be changed by a user according to the purpose of the test. Alternatively, a unique value may still be set for each test item. For example, in the example shown in FIG. 6, if the threshold value is set to 50, then a broken line 330 represents the threshold value. In this case, the variation in the parameter falls below the threshold value at a point in time 35, at which it is determined that the sufficient amount of absorbance data required for calculating the concentration is stored.

If there is a plurality of parameters involved, the threshold value is set for the variation in each of all parameters and, when the variations in all parameters fall below the respective threshold values, the control is passed onto step S65. Various examples are, however, conceivable for this condition for determination; specifically, the control may be passed onto step S65, if some of the multiple parameters fall below the threshold values.

If it is determined in step S55 that another data reading is available, the control is returned to step S10 and the next absorbance data is input. If the next absorbance data is not available, it is then determined that the parameter with sufficient accuracy is not obtained even with the lapse of a predetermined reaction time, so that the data is recorded as abnormal in step S60.

In step S65, the concentration of the substance to be measured is calculated using the parameter calculated in step S30. In the endpoint assay, the concentration is calculated through conversion from the absorbance at a specific point in time at which the absorbance no longer changes after the lapse of a sufficient amount of time. In the present invention, the parameter value calculated in step S30 is substituted for the approximate expression selected in step S5 and a value of the expression when time is varied to infinity is regarded as the absorbance after the lapse of the sufficient amount of time. Specifically, the absorbance to be obtained is a0 in (expression 1), (expression 2), and (expression 5), c in (expression 3), and d in (expression 4). According to the present invention, the concentration can be calculated when the parameter becomes a constant value even with the absorbance varying. This permits highly accurate measurement within a shorter reaction time as compared with the related art. A known method using a calibration curve, for example, may be used for converting the absorbance obtained from the parameter to corresponding concentration of the substance to be measured.

In the rate assay, the parameter value calculated in step S30 is substituted for the approximate expression selected in step S5. Then, a gradient of a straight line portion is calculated and the gradient obtained is translated to a corresponding concentration value of the substance to be measured. Specifically, a value of a parameter a in (expression 6) to (expression 11) corresponds to the gradient of the straight line portion. In the expression of an ordinary curve like (expression 12), a portion with the smallest change in gradient is considered to be the straight line. Specifically, a second-order derivative $g''(t, \phi)$ of time is obtained and a point in time ta at which an absolute value of $g''(t, \phi)$ is the smallest is regarded as the straight line. A first-order derivative with respect to time at ta $g'(ta, \phi)$ is the gradient of the straight line. In the rate assay, a curved portion in the beginning of the reaction has different lengths and shapes according to the condition and, in the related art, it is difficult to determine the straight line portion, which makes it difficult to set a reaction time optimum for determining the straight line portion. According to the present invention, the gradient of the straight line portion in the rate assay can be easily determined and the reaction time can be optimized. A known method using a calibration curve, for example, may be used for converting the gradient of the straight line portion to corresponding concentration of the substance to be measured.

In step S70, an error relative to the concentration value obtained is calculated. As described with reference to step S45, in the beginning of the reaction during which the number of absorbance data readings available remains small, the error contained in the data contributes to a greater error contained in the estimated parameter. As the number of absorbance data readings increases with time, random errors contained in the absorbance data are offset, resulting in a smaller error contained in the estimated parameter. As a result, the smaller the number of absorbance data readings, the greater the error contained in the concentration value finally arrived at through conversion, and the greater the number of readings, the smaller the error.

Figure 7:
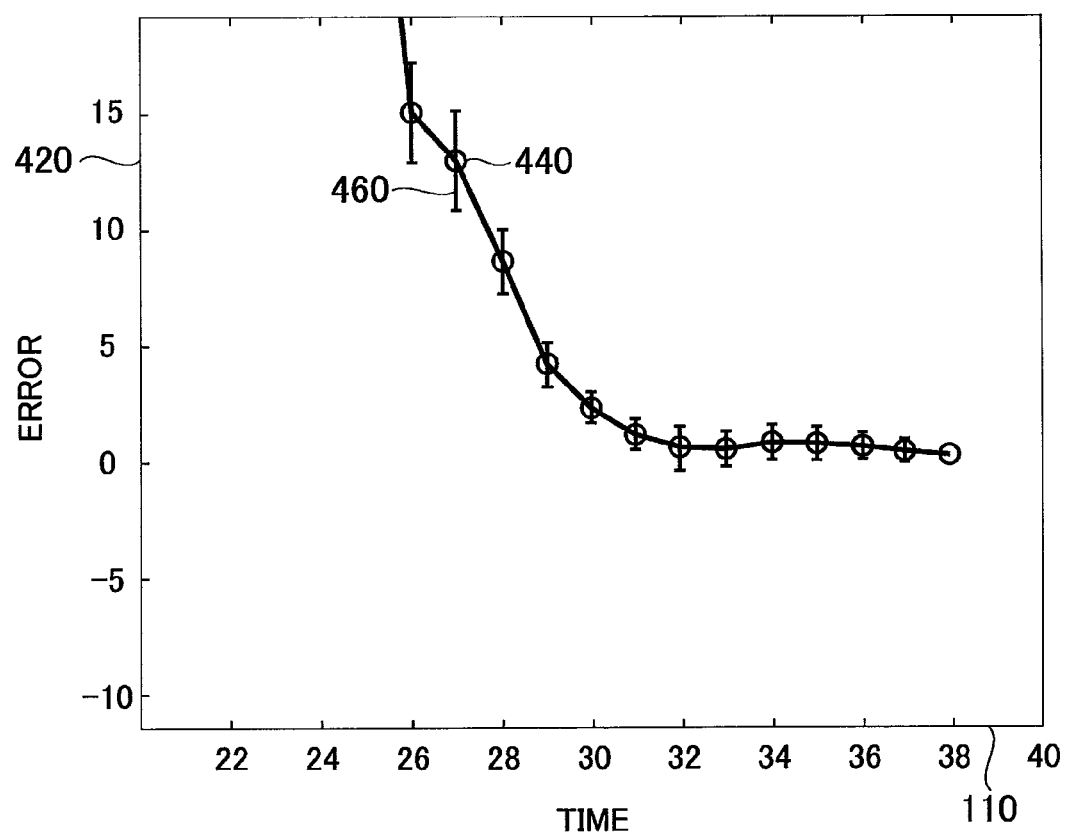
FIG. 7 is a graph showing a distribution of errors in calculated concentration values.

FIG. 7, for example, shows a distribution of errors in the concentration value in a mid-point in time relative to the concentration value calculated when all absorbance data readings are used. FIG. 7 shows schematically a result of errors in the concentration value calculated at each point in time in measurements taken 20 times of an accuracy control substance with a known concentration. In FIG. 7, an abscissa 110 represents time elapsed, while an ordinate 420 represents errors. A symbol 440 represents a mean value of a distribution of errors at each point in time and a line segment 460 represents standard deviation of errors at each point in time. Both the mean value and the standard deviation of errors are smaller as time elapses.

A distribution of errors of the concentration values calculated at each point in time using a large plurality of data readings is examined in advance and a relationship between points in time and the error distribution is stored as a table. The mean value and the standard deviation of errors at each point in time, for example, are stored in the table. In step S70, the error at the point in time at which the concentration value is calculated is obtained from the table stored of the relationship between points in time and errors. For example, the user is able to identify the range of errors of measurements using the mean value and a dispersion value displayed. In addition, a display of the distribution of errors at each point in time stored in the table serves as reference information when a minimum number of times the parameter is calculated, used in step S40 or the threshold value of parameter variations used in step S50 is to be set.

In the first embodiment described heretofore, the parameter contained in the expression is obtained a plurality of times during the reaction time from the absorbance data and, based on the magnitude of the variation with time in the parameter, it is determined whether time required for calculating the concentration elapses. The reaction time can therefore be automatically determined even when it is unknown specifically how much reaction time should be set. The reaction time can also be determined even if the optimum reaction time varies according to the type of the substance to be measured or the reagent to be used.

The error is estimated corresponding to the number of time-series data readings used, specifically, the reaction time, so that the apparatus user can identify quantitatively how much reaction time set results in how much error. An optimum reaction time can also be set according to the item or purpose.

Using an item of TG (neutral fat) as an example, a specific method for calculating the concentration through rapid measurement will be described.

Figure 8:
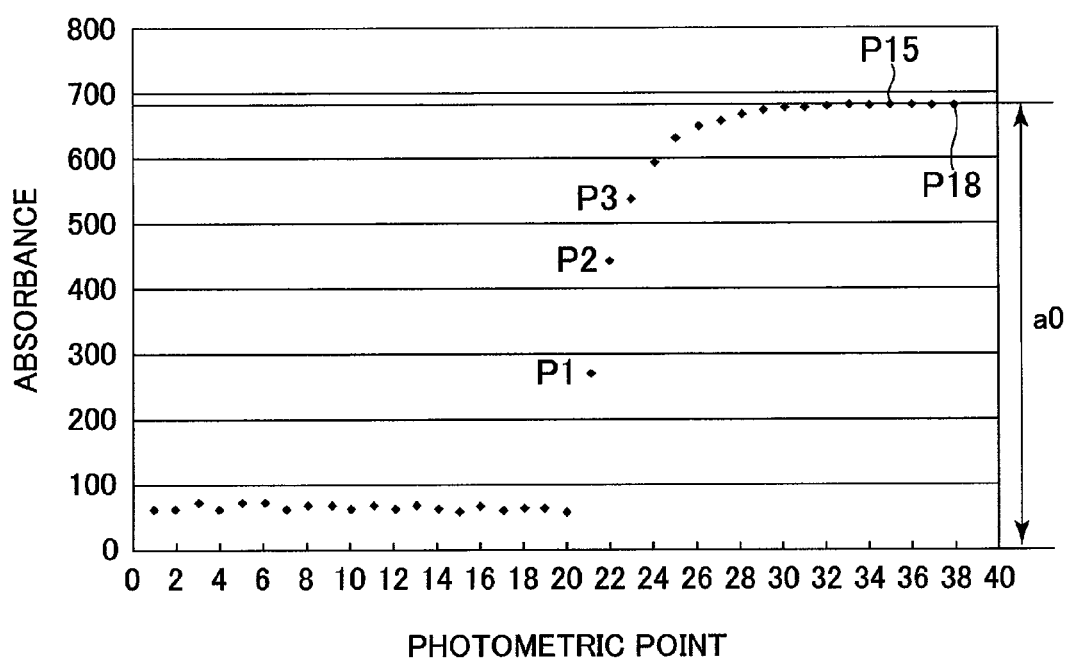
FIG. 8 is a graph showing reaction process data when TG is measured.

The endpoint assay of the two-reagent reaction was used for measuring TG. A reaction process thereof exhibits, as shown in FIG. 8, a pattern in which the absorbance increases after a second reaction is added and becomes substantially constant as the reaction progresses over a predetermined period of time. Preferably, an expression that accurately approximates this reaction process is examined in advance or selected and set when a calibrator is measured. Alternatively, calculations are performed individually and in parallel using multiple expressions of from (expression 1) to (expression 5) and which approximate expression should be used to calculate the concentration in the portion to determine concentration calculation may be determined from a magnitude of a residual error (a difference between a value of absorbance obtained using the approximate expression and a value of absorbance obtained through actual measurement).

In the first embodiment, (expression 1) is set in advance for the approximate expression used in rapid calculation of TG when a reagent R is used. In the automatic analyzer having arrangements as shown in FIG. 2, a sample and a reagent are applied to the reaction vessel 21 in FIG. 2 and are then mixed together. A reaction of a process for generating a substance to be measured is then started. Let P1 be the first photometric point after the absorbance starts rising. Then, in this analyzer, for example, absorbance is to be obtained from P1 to P18 as time elapses (FIG. 8). Calculation of the approximate expression requires absorbance values at two or more points, so that the calculations of the photometric points required for concentration are started at the measuring time point of P2.

Calculation of the approximate expression is performed each time absorbance is measured, using measurements at points P1 and P2, and points P1 to P3, and at P2 to P4, P1 to P5, and so on.

Values of parameters calculated through approximate calculation, for example, a final absorbance value A (a0) calculated by the approximate expression are stabilized as the number of photometric points increases as a result of improved approximation accuracy as shown in FIG. 5. A parameter k other than A, or an absorbance x (t) at any given point in time t may be used as the numeric value for determination. Referring, for example, to FIG. 6, as a criterion for evaluating stability of parameter values, dispersion is obtained for five calculated parameter values (P2 to P6). As the parameter is stabilized, a value of dispersion thereof is smaller. A threshold value is set at, for example, the value of dispersion and, if the dispersion is equal to, or less than, the threshold value, it is determined that the parameter is stable. Then, using the approximate expression and the parameter value at that point in time, the measured value is estimated and calculated. Referring to FIG. 6, it is here determined that the parameter is stable when the dispersion value is 10 or less and the concentration is calculated from the approximate expression at photometric points P1 to P15 (photometric point 35).

The following expression is typically used to calculate the concentration in automatic analyzers.

$Cx=\{k \times (\text{absorbance of specimen} - \text{absorbance of standard solution 1})\} \times \text{apparatus constant}$ (Expression 13)

Where, k is a k factor to be obtained from a calibration result. The concentration Cx to be obtained of the substance to be measured can be obtained from the absorbance a0 at any given point in time or when the reaction is in equilibrium. Alternatively, an absorbance Ct at a normal measurement end point in time is calculated from the approximate expression and output as an estimated value Cm.

Second Embodiment

A biochemical automatic analyzer according to a second embodiment of the present invention is configured schematically as shown in FIG. 2, as in the first embodiment. Operation of all elements but a control section 13 is the same as that of the first embodiment and descriptions therefor will be omitted.

Figure 9:
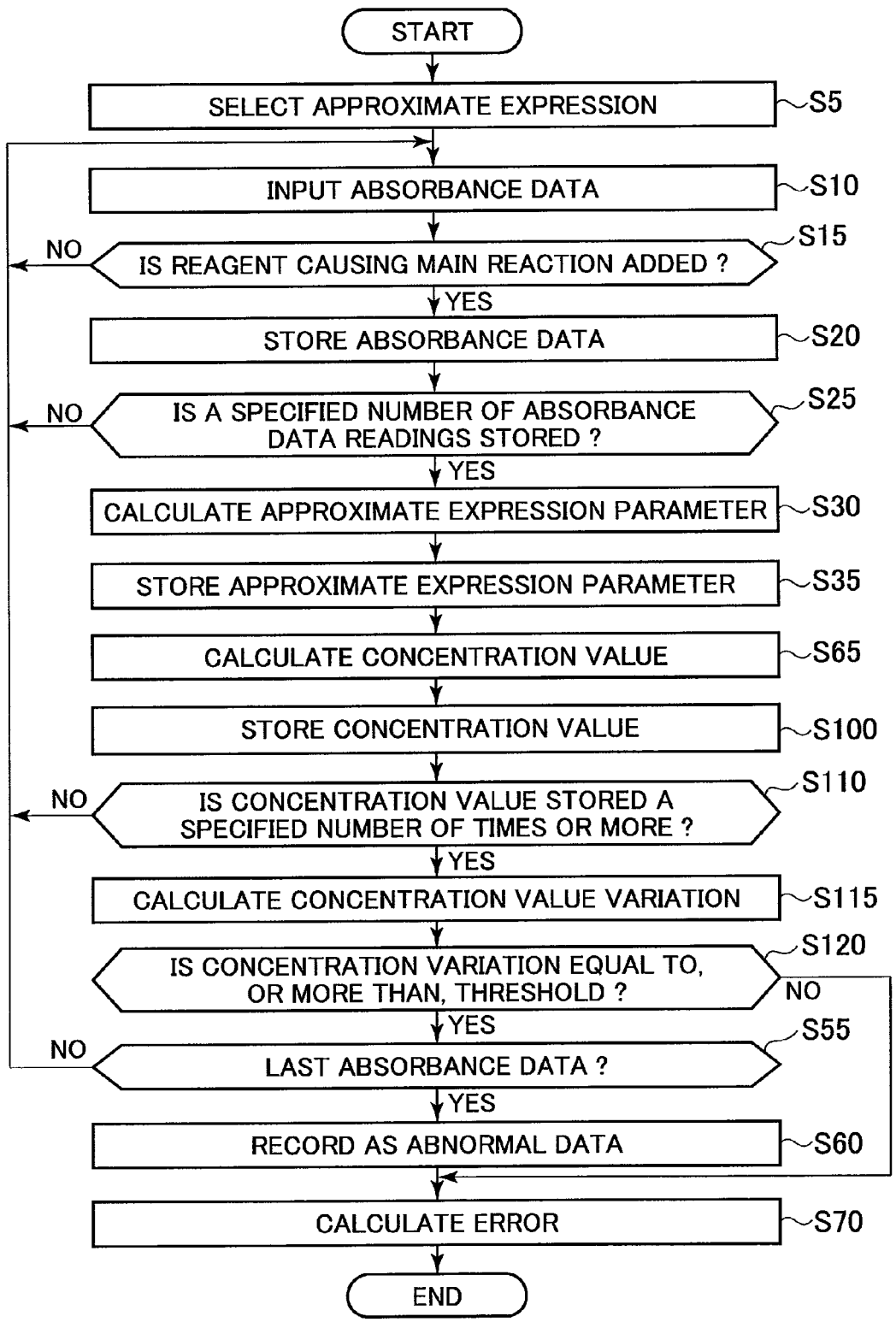
FIG. 9 is a flow chart showing processes performed according to a second embodiment of the present invention.

Processes for conversion of absorbance to corresponding concentration of the specimen in the control section in the second embodiment will be described in detail below with reference to FIG. 9. Processes identified by the same reference numerals as those in FIG. 1 are the same as those identified by the same reference numerals in FIG. 1 and detailed descriptions therefor will be omitted in the following.

Processes in steps S5, S10, S15, S20, S30, and S35 are the same as those in the first embodiment shown in FIG. 1. In this embodiment, after the parameter is calculated in step S35, a value of concentration of the substance to be measured is calculated using the calculated parameter in step S65. A detailed process for calculating the value of concentration from the parameter is the same as that in step S65 described with reference to the first embodiment. The calculated concentration value is stored in step S100.

In step S110, it is determined whether the concentration value is calculated and stored a number of time sufficient to fix the calculated concentration value as a final measurement. As described earlier with reference to step S40 in the first embodiment, generally, the smaller the number of observed data readings, the greater the number of errors contained in the calculated concentration value. In this embodiment, therefore, to prevent a concentration value containing a large number of errors from being output, a minimum number of times required for calculating concentration to be fixed as the final measurement is established. Then, in step S110, it is determined whether the concentration value is calculated the set number of time or more. If it is determined that the concentration value is not calculated the required number of times, the control is returned to step S10 and the next absorbance data is input. If it is determined that the concentration value is calculated the required number of times, the control is passed onto step S120.

In step S115, a magnitude of a variation with time in the calculated concentration value is calculated. In the present invention, processes are repeated in which the absorbance is measured after the reaction is started, the expression parameter is obtained, and the concentration value is calculated. The calculation of the expression parameter is to estimate the expression parameter such that the parameter matches with the observed absorbance as much as possible. In the beginning of the reaction during which the number of absorbance data readings available remains small, however, the error contained in the data contributes to a greater error contained in the estimated parameter; as a result, the error contained in the calculated concentration value is great. As the number of absorbance data readings increases with time, random errors contained in the absorbance data are offset, resulting in a smaller error contained in the estimated parameter and in the calculated concentration value. As a result, in the beginning of the reaction, the value of the concentration value calculated each time is varied as affected by the error contained in the absorbance. As the number of data readings increases, however, the variation in the concentration value becomes small and converges to an optimum value. Such variations with time are noted in the concentration value in the same manner as with the parameter value shown in FIG. 5.

In step S115, the magnitude of such a variation with time in the concentration value is digitized. Various methods can be used for digitizing the variation with time in the concentration value. For example, a difference from a concentration value immediately before a current one, dispersion of several concentration values, or a difference between a maximum value and a minimum value of several concentration values may be used. Use of dispersion, for the variation with time in the concentration value, of a total of five concentration values of a current one at a specific point in time and four preceding ones before the current one exhibits the same change as the variations in the parameter shown in FIG. 6.

In step S120, the variation with time in the concentration value obtained in step S115 is compared with a predetermined threshold value. If the variation with time in the concentration value is equal to, or less than, the predetermined threshold value, it is then determined that a sufficient amount of absorbance data required for calculating the concentration of the substance to be measured has been stored, so that the control is passed onto step S70 in which an error is calculated. If the variation with time in the concentration value is greater than the predetermined threshold value, it can then be considered that the sufficient amount of absorbance data required for calculating the concentration is yet to be stored. The control is then passed onto step S55 in which it is determined whether another data reading is available. The threshold value for comparison of the variation in the concentration value is set in advance so as to achieve required measurement accuracy according to the purpose of the apparatus. It is noted that an arrangement may be made so as to allow the threshold value to be changed by a user according to the purpose of the test. Alternatively, a unique value may still be set for each test item.

Processes performed in steps S55, S60, and S70 are the same as those identified by the same reference numerals in the first embodiment and descriptions therefor will be omitted.

In the second embodiment described above, the parameter contained in the expression is obtained and a concentration value is calculated a plurality of times during the reaction time from the absorbance data and, based on the magnitude of the variation with time in the concentration value, it is determined whether time required for calculating the concentration elapses. The reaction time can therefore be automatically determined even when it is unknown specifically how much measurement time should be set. The reaction time can also be determined even if the optimum reaction time varies according to the type of the substance to be measured or the reagent to be used.

The error is estimated corresponding to the number of time-series data readings used, specifically, the reaction time, so that the apparatus user can identify quantitatively how much reaction time set results in how much error. An optimum reaction time can also be set according to the item or purpose.

Third Embodiment

A biochemical automatic analyzer according to a third embodiment of the present invention is configured schematically as shown in FIG. 2, as in the first embodiment. Operation of all elements but a control section 13 is the same as that of the first embodiment and descriptions therefor will be omitted.

Figure 10:
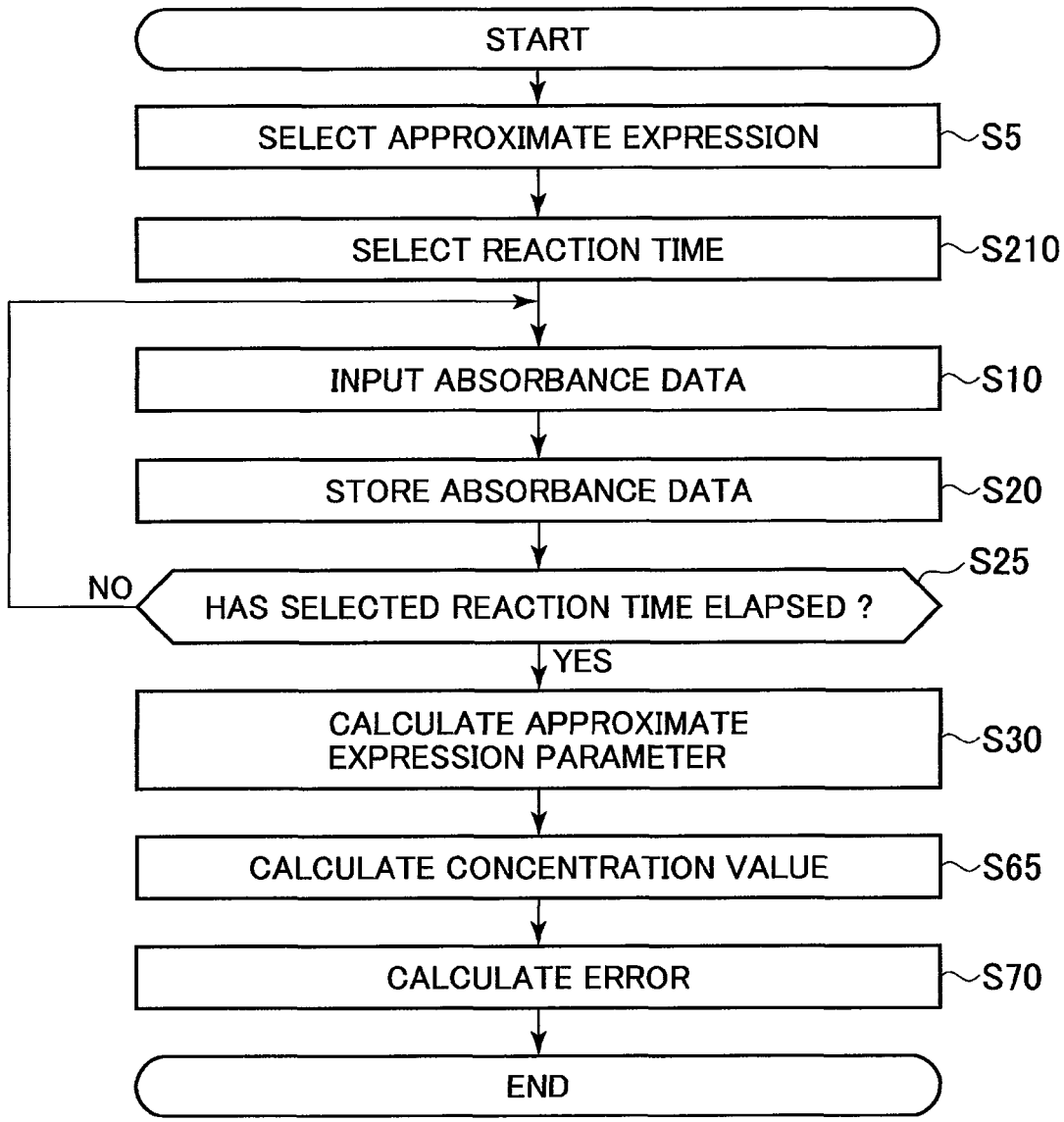
FIG. 10 is a flow chart showing processes performed according to a third embodiment of the present invention.

Processes for conversion of absorbance to corresponding concentration of the specimen in the control section in the third embodiment will be described in detail below with reference to FIG. 10. Processes identified by the same reference numerals as those in FIG. 1 are the same as those identified by the same reference numerals in FIG. 1 and detailed descriptions therefor will be omitted in the following.

The approximate expression is selected in step S5 and the reaction time is selected in step S210. Referring to FIG. 11, a control section 13 stores a table 500 that describes an optimum approximate expression and an optimum reaction time for each combination of a test item (substance to be measured) and a reagent to be used. A column 510 describes test items and a column 520 describes types of reagents. The test items represent the substances to be measured. A column 530 describes the optimum approximate expression for the test item and the type of reagent concerned. A column 540 describes the optimum reaction time. From the combination of the test item and the reagent, the optimum approximate expression is selected using the table 500 in step S5 and similarly the optimum reaction time is selected using the table 500 in step S210. Contents of the table may be arranged to be modifiable by the user.

In step S10, absorbance data is input from a photometry mechanism 8 and the absorbance data is stored in step S20. In step S25, it is determined whether the reaction time selected in step S210 has elapsed. If it is determined that the reaction time is yet to elapse, the control is returned to step S10 and next absorbance data is input. If it is determined that the reaction time has elapsed, the control is passed onto step S30.

In S30, the parameter of the approximate expression selected in step S5 is calculated using the stored absorbance data. Further in step S65, a value of the parameter calculated in step S30 is translated to corresponding concentration of a chemical component of the substance to be measured. In step S70, an error corresponding to the reaction time is calculated.

Figure 12:
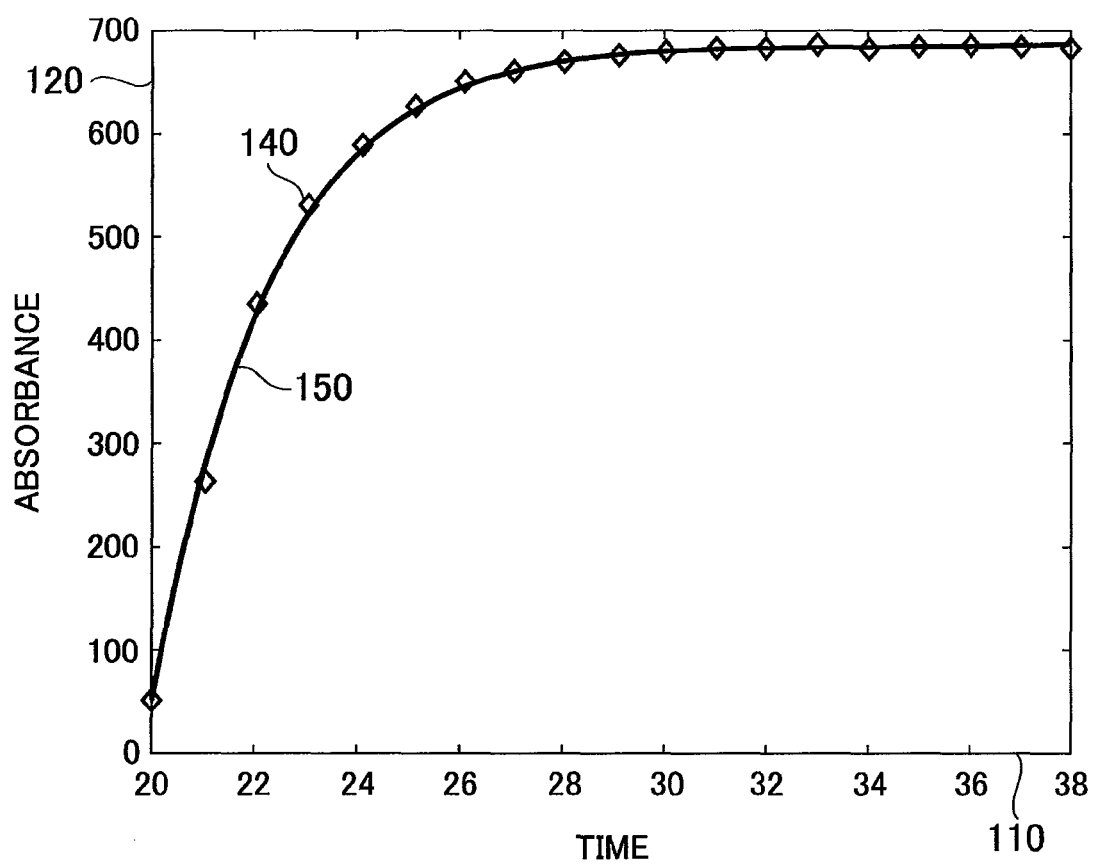
FIG. 12 is a graph showing changes in absorbance with time in measurement taken according to the endpoint assay and changes in absorbance obtained by the approximate expression.

In the third embodiment described above, a plurality of expressions is stored, each expression including one or a plurality of parameters describing changes with time in absorbance, and an optimum expression is selected from the combination of the substance to be measured and the reagent. This allows the change with time in absorbance to be expressed by an expression more accurately than the related art, so that an optimum reaction time can be set even more easily. For example, FIG. 12 is an example in which the absorbance data shown in FIG. 8 showing a test item TG (neutral fat) measured with the endpoint assay is used to find the parameter value of (expression 1) and an absorbance change curve (reaction process curve) obtained by substituting the obtained parameter value for (expression 1) and actual absorbance data plotted on the same graph. An abscissa 110 represents time elapsed, while an ordinate 120 represents absorbance. A symbol 140 represents absorbance actually measured at each point in time and a curve 150 represents a change with time in absorbance calculated with the approximate expression. In this example, the change with time in the absorbance actually obtained matches well with the change with time expressed by (expression 1).

Figure 13:
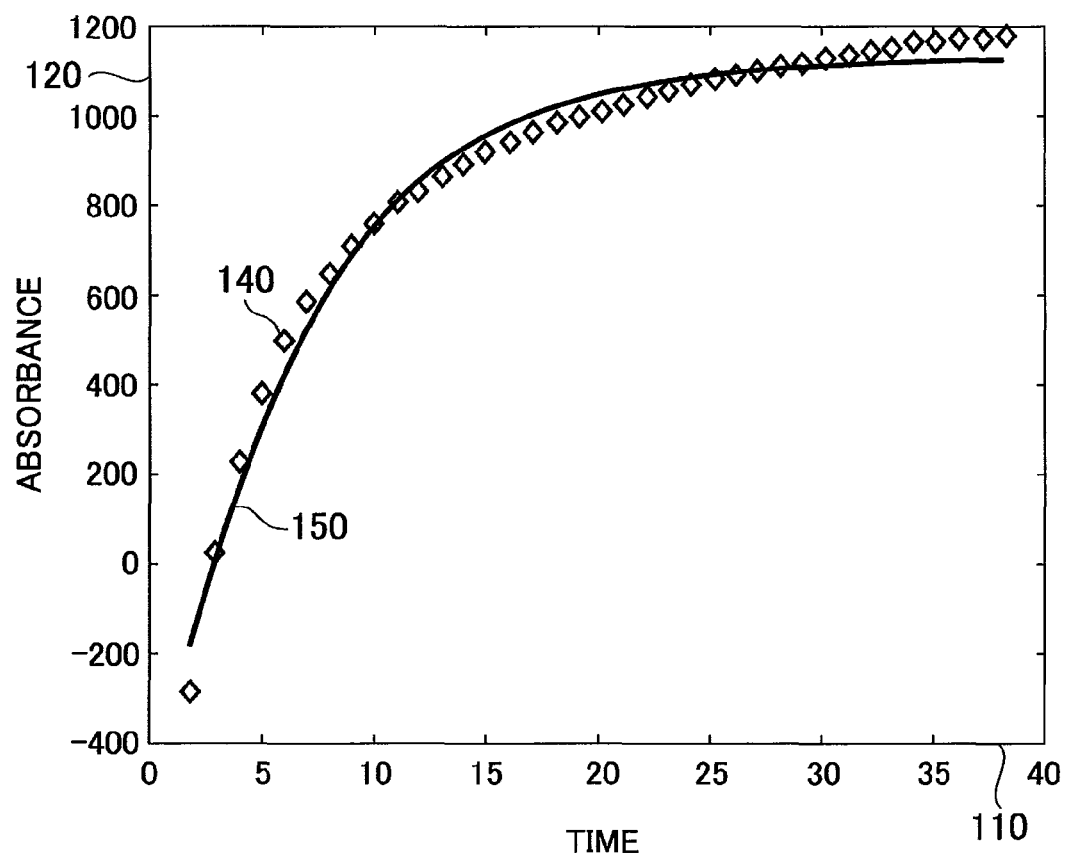
FIG. 13 is a graph showing changes in absorbance with time in measurement taken according to the endpoint assay and changes in absorbance obtained by the approximate expression.
Figure 14:
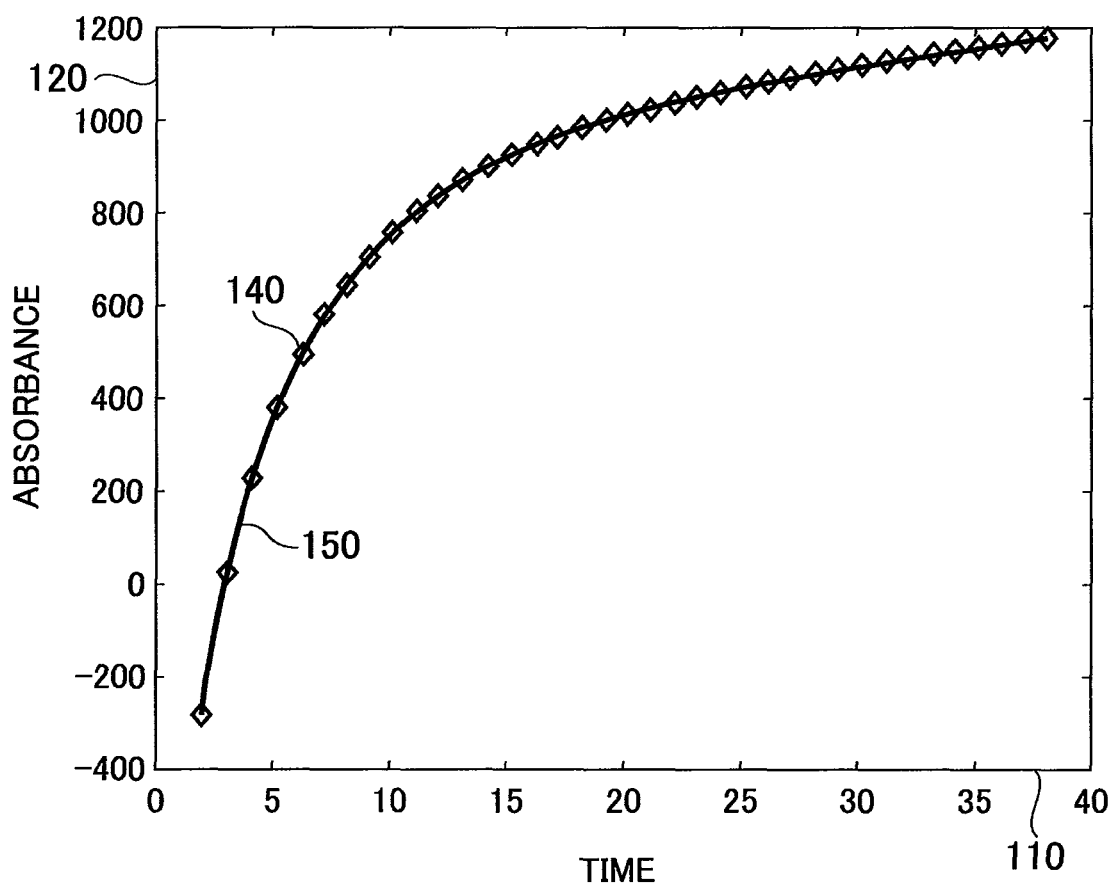
FIG. 14 is a graph showing changes in absorbance with time in measurement taken according to the endpoint assay and changes in absorbance obtained by the approximate expression.

FIG. 13 shows a result of processing performed in the same manner using absorbance data of another test item TP (total protein). As evident from the figure, there is a large error between absorbance measured actually and absorbance calculated with the approximate expression after a sufficient time has elapsed. This example reveals that (expression 1) is not suitable for expressing the change with time in the absorbance of this test item. FIG. 14 shows a result of processing performed using (expression 2) for this absorbance data. The figure shows that (expression 2) is suitable for expressing the change with time in the absorbance data of this test item.

In the rate assay, the activity value and related data of the enzyme as the substance to be measured is obtained from gradient of a straight line portion in the change in absorbance; however, application of (expression 1) makes it difficult to detect clearly the straight line portion. Use of (expression 7) to (expression 11) for items measured with the rate assay allows the gradient of the straight line portion to be detected easily as a value of the parameter a. If (expression 12) is used, the gradient of the straight line portion can be calculated easily as a first-order derivative with respect to time of a point at which a second-order derivative with respect to time is the smallest.

As described above, one type of expression cannot express the change with time in absorbance for various combinations of test items and reagents with sufficiently high accuracy. By selectively using a plurality of expressions as in this embodiment, the change with time in absorbance can be expressed with sufficiently high accuracy for various combinations of test items and reagents, so that highly accurate results can be obtained within a short reaction time.

Fourth Embodiment

A fourth embodiment shares the same system configuration shown in FIG. 2 and the process steps shown in FIG. 1 with the first embodiment. Only the approximate expression selected in step S5, the method for calculating the approximate parameter in step S30, and the calculation of the concentration in step S65 shown in FIG. 1 differ and processes of these steps will be described in detail.

In the first embodiment, expressions that represent absorbance x as a function of time t are used for the expressions that can be selected in step S5. In this embodiment, a differential equation is used as the expression. Differential equations are very often used for illustrating the change in absorbance with time theoretically and a theoretical expression can be directly used in this embodiment. For example, let t denote time, x denote absorbance, $\Sigma\{\ \}$ denote a symbol representing a sum of all values, each value being obtained by substituting i in $\{\ \}$ for a value of 1 to n, n denote a whole number of 1 or more, fi(t, x) denote a function including t, x, or a time derivative of any order of x, including a constant, and qi denote a parameter. Then, a differential equation of a format expressed by the following expression can be used.

$$\Sigma\{qi*fi(t,x)\}=0 \qquad \text{(Expression 13)}$$

A differential equation shown in (expression 14) may also be used as a special case of (expression 13). Where, x[n](t) denotes an nth-order time derivative of absorbance x at time t and p and pi denote parameters.

$$p+\Sigma\{pi*x[n](t)\}=0 \qquad \text{(Expression 14)}$$

More specifically, for example, differential equations as shown below may be used, where, x(t)^2 denotes a square of x(t).

$$p+p0*x(t)+p1*x[1](t)=0 \qquad \text{(Expression 15)}$$

$$p+p0*x(t)+p1*x[1](t)+p2*x[2](t)=0 \qquad \text{(Expression 16)}$$

$$q2*x(t)^2+q3*x[1](t)=0 \qquad \text{(Expression 17)}$$

$$q1*x(t)+q2*x(t)^2+q3*x[1](t)=0 \qquad \text{(Expression 18)}$$

$$q0+q1*x(t)+q2*x(t)^2+q3*x[1](t)=0 \qquad \text{(Expression 19)}$$

In step S30, values of the parameters included in (expression 13) and (expression 14) are determined using the stored absorbance data. Absorbance is stored as time-series data, so that the time derivative can be approximately calculated by calculating a difference. Values corresponding to fi(t, x) in (expression 13) and to x[n](t) in (expression 14) at a point in time t at which the absorbance is measured can therefore be obtained. Given values of these at a plurality of points in time, (expression 13) and (expression 14) can be expressed in a linearly-combined format of fi(t, x) and x[n](t), respectively, so that values of parameters p, pi, and qi can be easily obtained through the least squares method. As an example, a case will be described in which the change in absorbance x with time is expressed by an expression given in (expression 15). It is also assumed that the absorbance is measured m+1 times to obtain absorbance of x0 to xm. (Expression 15) may be transformed into a format of the following expression, when x(t) is the left-hand side and the remaining terms of (expression 15) are the right-hand side.

$$x(t)=r1*x[1](t)+r \qquad \text{(Expression 20)}$$

In this case, as a quantity corresponding to the first-order time derivative, m−1 difference values of y1 to y(m−1) are obtained through, for example, calculations of y1=(x2−x0)/(2*h) and y2=(x3−x1)/(2*h). When xi and yi are substituted for x(t) and x[1](t) in (expression 20), (expression 20) can be expressed by (expression 21). Where, i=1 to m−1.

$$xi=p1*yi+p \qquad \text{(Expression 21)}$$

In reality, a relationship expressed by (expression 20) does not match exactly with absorbance observed, so that, in (expression 21), a value of the right-hand side does not match. Parameters r1 and r are therefore established using the least squares method so that a difference between the right-hand side and the left-hand side is minimal. Now, let X denote a vector formed by arranging xi vertically, A denote an (m−1)-by-2 matrix shown below, and R=(r1, r)'. Then, the relationship expressed by (expression 21) is expressed by (expression 22). Where, a symbol ' denotes transposition.

$$\begin{matrix} y1 & 1 \\ y2 & 1 \\ y3 & 1 \\ \vdots & \vdots \\ y(m-1) & 1 \end{matrix} \quad \text{(Expression 22)}$$

$$X = AR$$

A least squares solution can be obtained with (expression 23) by solving a characteristic equation of (expression 22). Where, inv( ) denotes an inverse matrix of the matrix in ( ).

$$R = \{\text{inv}(A'A)\}A'X \quad \text{(Expression 23)}$$

When the relationship between absorbance and time is to be expressed, the number of parameters to be obtained is generally smaller in an expression using a differential equation than in an expression using a function of t. Additionally, when a differential equation is expressed by a linearly-combined format of a function of the absorbance data reading as in (expression 13) and (expression 14), the parameters can be easily calculated through the least squares method as described above.

In step S65, the concentration of the substance to be measured is calculated using the parameter value obtained in step S30. In the endpoint assay, the absorbance becomes a predetermined value after the lapse of a sufficient period of time. Specifically, no change with time is involved, so that the time derivative is zero. The absorbance that has reached the predetermined value after the lapse of the sufficient period of time can therefore obtained from the value of x(t) when 0 is used for all of x[n](t), where n≥1. For example, setting x[1](t)=0 and x[2](t)=0 in (expression 15) and (expression 16), we have x=−p/p0, so that this value is determined to be the absorbance after the lapse of the sufficient period of time. The concentration of the substance to be measured is translated from this absorbance using, for example, a calibration curve.

In the rate assay, when the sufficient period of time has elapsed, the absorbance changes linearly with respect to time and the concentration of the substance to be measured is calculated from the gradient of this straight line. When the sufficient period of time has elapsed, the value of x[1](t) when 0 is used for all of x[n](t), where n≥2, can thus be determined to be the gradient of the change with time in absorbance after the lapse of the sufficient period of time. A value of concentration of the substance to be measured is translated from this gradient using, for example, a calibration curve.

As described above, in the fourth embodiment, a differential equation is used as the expression representing the change in absorbance with time, so that a differential equation derived from chemical kinetics can be directly applied. Other effects that can be achieved are to achieve a reduced number of parameters and to facilitate calculation of the least squares method to determine parameters as compared with the approach in which the absorbance is expressed as a function of time t.

Fifth Embodiment

A biochemical automatic analyzer according to a fifth embodiment of the present invention is configured schematically as shown in FIG. 2, as in the first embodiment. Operation of all elements but a control section 13 is the same as that of the first embodiment and descriptions therefor will be omitted.

Figure 15:
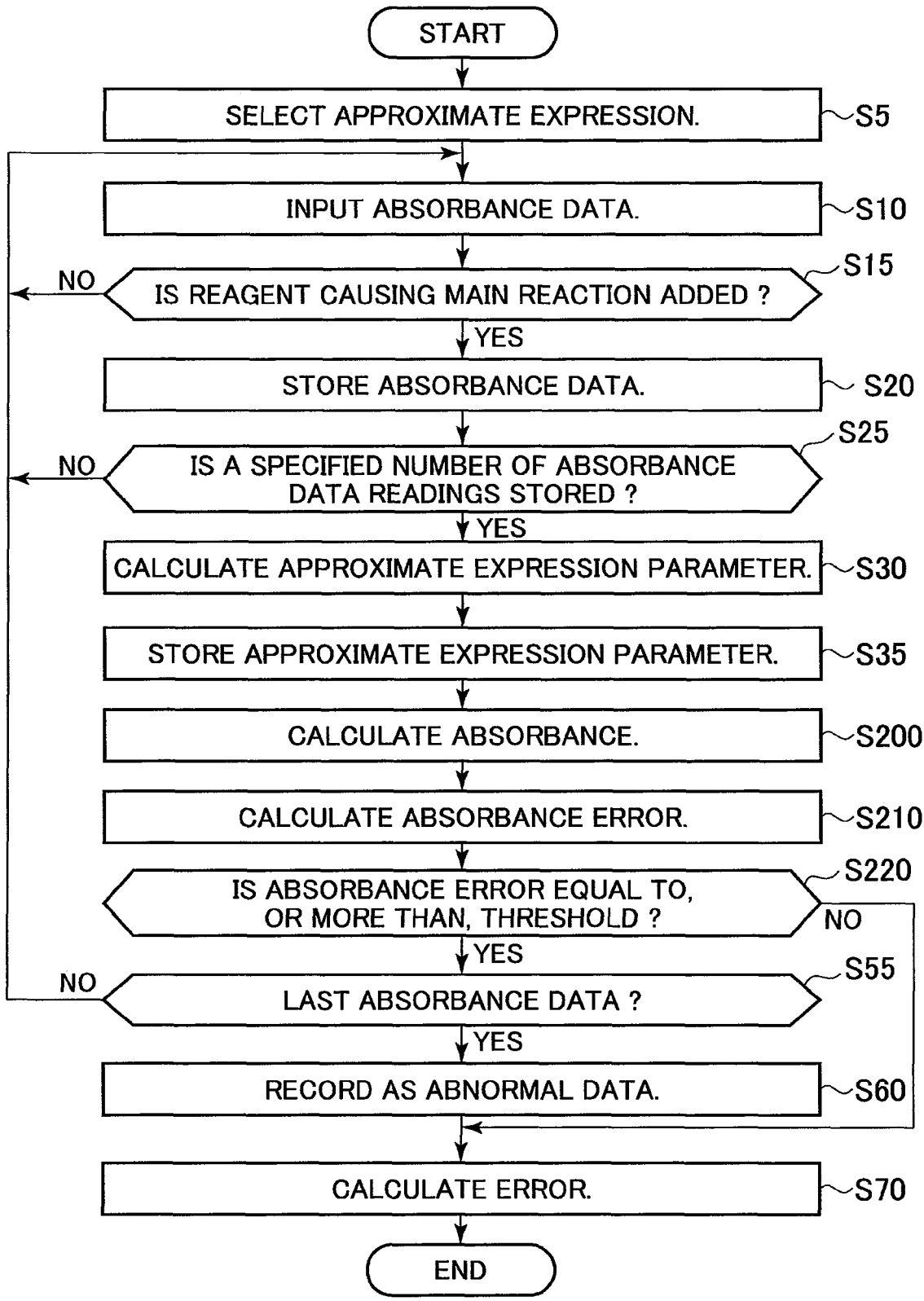
FIG. 15 is a flow chart showing processes performed according to a fifth embodiment of the present invention.

Processes for conversion of absorbance to corresponding concentration of the specimen in the control section in the fifth embodiment will be described in detail below with reference to FIG. 15. Processes identified by the same reference numerals as those in FIG. 1 are the same as those identified by the same reference numerals in FIG. 1 and detailed descriptions therefor will be omitted in the following.

Processes in steps S5, S10, S15, S20, S30, and S35 are the same as those in the first embodiment shown in FIG. 1. In this embodiment, after the parameter is calculated in step S35, the calculated parameter is substituted in the approximate expression in step S200 to thereby calculate an estimated value of concentration at a current point in time using the approximate expression.

In step S210, an error is calculated between the estimated value of the current absorbance obtained in step S200 and the absorbance actually measured and input in step S10.

In step s220, the error in the absorbance obtained in step S210 is compared with a predetermined threshold value. If the variation with time in the concentration value is equal to, or less than, the predetermined threshold value, it is then determined that a sufficient amount of absorbance data required for calculating the concentration of the substance to be measured has been stored, so that the control is passed onto step S70 in which an error is calculated. If the variation with time in the concentration value is greater than the predetermined threshold value, it can then be considered that the sufficient amount of absorbance data required for calculating the concentration is yet to be stored. The control is then passed onto step S55 in which it is determined whether another data reading is available. The threshold value for comparison of the error in the concentration value is set in advance so as to achieve required measurement accuracy according to the purpose of the apparatus. It is noted that an arrangement may be made so as to allow the threshold value to be changed by a user according to the purpose of the test. Alternatively, a unique value may still be set for each test item.

Processes performed in steps S55, S60, and S70 are the same as those identified by the same reference numerals in the first embodiment and descriptions therefor will be omitted.

In the fifth embodiment described above, the parameter contained in the approximate expression is obtained during the reaction time from the absorbance data and an absorbance estimated value at a point in time at which the absorbance is measured is obtained from the approximate expression. Further, an error between the estimated value and the measured value of absorbance. The longer the reaction time and the more the absorbance data readings, the higher the accuracy in approximation and the smaller the error. It can therefore be determined whether a period of time required for calculating the concentration has elapsed based on the magnitude of the error. The reaction time can be automatically determined even when it is unknown specifically how much measurement time should be set. The reaction time can also be determined even if the optimum reaction time varies according to the type of the substance to be measured or the reagent to be used.

DESCRIPTION OF REFERENCE NUMERALS

1: sample disk
2: reagent disk

3: reaction disk
4: reaction tank
5: sampling mechanism
6: pipetting mechanism
7: mixing mechanism
8: photometry mechanism
9: rinsing mechanism
10: display section
11: input section
12: storage section
13: control section
14: piezoelectric element driver
15: mixing mechanism controller
16: sample vessel
17, 19: circular disk
18: reagent bottle
20: cool box
21: reaction vessel
22: reaction vessel holder
23: drive mechanism
24, 27: probe
25, 28: bearing shaft
26, 29: arm
31: fixing section
33: nozzle
34: vertical drive mechanism
110: axis representing elapsed time
120: axis representing absorbance
130: broken line indicating a point in time at which a reagent causing the main reaction is applied
140: symbol representing absorbance measured
150: change with time in absorbance calculated with an approximate expression
220: axis representing parameter values
240: symbol representing a parameter value calculated at each point in time
320: axis representing dispersion of parameter
330: broken line indicating a threshold value set for dispersion
340: symbol representing dispersion of parameters calculated at various points in time
420: axis representing an error in the concentration value
440: symbol representing a mean value of errors in the concentration value
460: symbol representing standard deviation of errors in the concentration value
500: table describing an optimum approximate expression and an optimum reaction time for each combination of a test item and a reagent to be used
510: column describing test items
520: column describing types of reagents
530: column describing types of approximate expressions
540: column describing reaction times

The invention claimed is:

1. An automatic analyzer comprising:
a storage device that stores a plurality of approximate expressions each representing changes over time of a plurality of reaction processes of a plurality of specimens and reagents, each of the approximate expressions being associated with a corresponding test item or one of the specimens;
a photometer which measures actual values of one of the reaction processes of one of the specimens and reagents in a reaction vessel at predetermined intervals; and
a computer connected to the storage mechanism and the photometer, and which is programmed to execute:
a parameter optimizing mechanism which optimizes one or more parameters of one of the approximate expressions associated with the one of the specimens in the reaction vessel to the actual values of the one of the reaction processes measured by the photometer whenever the actual values of the one of the reaction processes are measured at the predetermined intervals; and
a determining mechanism which converts changes in the one or more parameters, which are optimized by the parameter optimizing mechanism whenever the actual values of the one of the reaction processes are measured at the predetermined intervals, into a numeric value, and determines whether or not the numeric value falls within a predetermined range over time,
wherein a measured value of the one of the reaction processes is calculated from the optimized parameters of the one of the approximate expressions associated with the one of the reaction processes measured by the photometer when the determining mechanism determines the numeric value falls within the predetermined range.

2. The automatic analyzer according to claim 1, wherein the computer is further programmed to execute:
a measured value calculating mechanism to establish the one of the approximate expressions based on the parameters optimized by the parameter optimizing mechanism and calculating the measured value at an end of the one of the reaction processes using the established approximate expression, when the determining mechanism determines that the numeric value falls within the predetermined range the predetermined range, and
wherein the storage device further stores a plurality of calibration curves which are each associated with a corresponding test item or one of the specimens, and
wherein the measured value is converted to a concentration of a substance to be measured in the one of the specimens in the reaction vessel with one of the calibration curves associated therewith stored in the storage device.

3. The automatic analyzer according to claim 1, wherein:
the determining mechanism stores the predetermined range as a reference space, calculates a Mahalanobis distance based on a change in the parameters at a current point in time, and thereby determines that the predetermined range is reached.

4. The automatic analyzer according to claim 1, wherein:
the determining mechanism determines whether the numeric value falls within the predetermined range using a neural network.

5. The automatic analyzer according to claim 1, wherein the computer is further programmed to execute:
an approximate expression selecting mechanism to select the one of the approximate expressions from among the approximate expressions according to the substance to be measured or the reagents for the corresponding test item or specimen.

6. The automatic analyzer according to claim 1, wherein:
at least one of the approximate expressions is:

$$x = a_0 + a_1 * \exp(-k_1 * t) + a_2 * \exp(-k_2 * t),$$

where t denotes a measurement point in time, x denotes a calculated value, and * denotes a symbol representing multiplication; and
the parameters include $a_0$, $a_1$, $a_2$, $k_1$, and $k_2$.

7. The automatic analyzer according to claim 1, wherein:
at least one of the approximate expressions is:

$$x = a_0 + \Sigma\{a_i * \exp(-k_i * t)\},$$

where t denotes a measurement point in time, x denotes a calculated value, $\Sigma\{\ \}$ denotes a symbol representing a sum of all values, each value being obtained by substituting i in $\{\ \}$ for a value of 1 to n, n denotes a natural number, and * denotes a symbol representing multiplication; and the parameters include $a_0$, $a_i$, and $k_i$.

8. The automatic analyzer according to claim 1, wherein:
at least one of the approximate expressions is:

$$x = c + (1/(b_0 + b_1 * t)),$$

where t denotes a measurement point in time, x denotes a calculated value, and * denotes a symbol representing multiplication; and the parameters include $b_0$, $b_1$, and c.

9. The automatic analyzer according to claim 1, wherein:
at least one of the approximate expressions is:

$$x = d + (e/(\exp(r * t) + s)),$$

where t denotes a measurement point in time, x denotes a calculated value, and * denotes a symbol representing multiplication; and the parameters include d, e, r, and s.

10. The automatic analyzer according to claim 1, wherein:
at least one of the approximate expressions is:

$$x = a * t + b + h(t, \psi),$$

where t denotes a measurement point in time, x denotes a calculated value, $\psi$ denotes a plurality of parameters, and * denotes a symbol representing multiplication; and the parameters include a, b, and $\psi$ and a concentration of a substance to be measured is calculated from a value of a.

11. The automatic analyzer according to claim 1, wherein:
at least one of the approximate expressions is:

$$x = a * t + b + c_1 * \exp(-k_1 * t),$$

where t denotes a measurement point in time, x denotes a calculated value, and * denotes a symbol representing multiplication; and the parameters include a, b, $c_1$, and $k_1$.

12. The automatic analyzer according to claim 1, wherein:
at least one of the approximate expressions is:

$$x = a * t + b + \Sigma\{c_i * \exp(-k_i * t)\},$$

where t denotes a measurement point in time, x denotes a calculated value, $\Sigma\{\ \}$ denotes a symbol representing a sum of all values, each value being obtained by substituting i in $\{\ \}$ for a value of 1 to n, n denotes a natural number, and * denotes a symbol representing multiplication; and the parameters include a, b, $c_i$, and $k_i$.

13. The automatic analyzer according to claim 1, wherein:
at least one of the approximate expressions is:

$$x = a * t + b + e/(t + d),$$

where t denotes a measurement point in time, x denotes a measured value, and * denotes a symbol representing multiplication; and the parameters include a, b, d, and e.

14. The automatic analyzer according to claim 1, wherein:
at least one of the approximate expressions is:

$$x = a * t + b + w/\{\exp(u * t) + v\},$$

where t denotes a measurement point in time, x denotes a measured value, and * denotes a symbol representing multiplication; and the parameters include a, b, u, v, and w.

15. The automatic analyzer according to claim 1, wherein:
at least one of the approximate expressions is:

$$x = a * t + b + p * \log\{1 + q * \exp(r * t)\},$$

where t denotes a measurement point in time, x denotes a calculated value, and * denotes a symbol representing multiplication; and the parameters include a, b, p, q, and r.

16. The automatic analyzer according to claim 1, wherein:
at least one of the approximate expressions is:

$$x = g(t, \phi),$$

where t denotes a measurement point in time, x denotes a calculated value, and $\phi$ denotes a plurality of parameters;

the parameter are represented by $\phi$; and a concentration of a substance to be measured is calculated from a value of a first-order derivative $g'(t, \phi)$ with respect to time of the expression at t at which an absolute value of a second-order derivative $g''(t, \phi)$ with respect to time of the expression is the smallest.

17. The automatic analyzer according to claim 1, wherein:
the approximate expression is:

$$p_0 + \Sigma\{p_i * x[n](t)\} = 0,$$

where t denotes a measurement point in time, x denotes absorbance, x[n](t) denotes an nth-order time derivative of a measured value at time t, $\Sigma\{\ \}$ denotes a symbol representing a sum of all values, each value being obtained by substituting i in $\{\ \}$ for a value of 0 to n, n denotes a whole number of 1 or more, and * denotes a symbol representing multiplication; and the parameters include $p_0$ and $p_i$.

18. The automatic analyzer according to claim 1, wherein:
the approximate expression is:

$$\Sigma\{q_i * f_i(t, x)\} = 0,$$

where t denotes a measurement point in time, x denotes a measured value, $\Sigma\{\ \}$ denotes a symbol representing a sum of all values, each value being obtained by substituting i in $\{\ \}$ for a value of 0 to n, n denotes a whole number of 1 or more, fi(t, x) denotes a function including t, x, or a time derivative of any order of x, including a constant, and * denotes a symbol representing multiplication; and the parameters are $q_i$.

19. An automatic analyzer comprising:

a storage device which stores a plurality of approximate expressions each representing changes in a plurality of reaction processes of a plurality of specimens and reagents over time, each of the approximate expressions being associated with a corresponding test item or one of the specimens;

a photometer which measures one of the reaction processes of one of the specimens and reagents in a reaction vessel at predetermined intervals and outputs a plurality of actual values thereof; and a computer connected to the storage mechanism and the photometer to receive the actual values at predetermined intervals, and which is programmed to execute:

a parameter optimizing mechanism which, when the actual values are measured for the one of the reaction processes at the predetermined intervals, optimizes one or more parameters of one of the approximate expressions associated with the one of the specimens in the reaction vessel to fit the actual values of the one of the reaction processes measured by the photometer;

a substance-to-be-measured concentration calculating mechanism which, when the actual values are measured for the one of the reaction processes at the predetermined intervals, calculates concentrations of a substance to be measured in the one of the specimens in the reaction vessel based on the parameters optimized by the parameter optimizing mechanism;

a determining mechanism which, when the actual values are measured for the one of the reaction processes at the predetermined intervals, determines whether or not a difference between a last one of the concentrations of the substance calculated by the substance-to-be-measured concentration calculating mechanism and a previous one of the concentrations of the substance falls within a predetermined range over time; and an output mechanism which outputs the last one of the concentrations of the substance to be measured when the determining mechanism determines that the difference falls within the predetermined range.

20. An automatic analyzer comprising:

a storage device that stores a plurality of approximate expressions each representing changes in a plurality of reaction processes of a plurality of specimens and reagents over time, each of the approximate expressions being associated with a corresponding test item or one of the specimens;

a photometer which measures one of the reaction processes of one of the specimens and reagents in a reaction vessel at predetermined intervals and outputs a plurality of actual values thereof; and a computer connected to the storage mechanism and the photometer to receive the actual values at the predetermined intervals, and which is programmed to execute:

a parameter optimizing mechanism which, when the actual values are measured for the one of the reaction processes at the predetermined intervals, optimizes one or more parameters of one of the approximate expressions associated with the one of the specimens in the reaction vessel to fit the actual values of the one of the reaction processes measured by the photometer;

a substance-to-be-measured concentration estimating mechanism which, when the actual values are measured for the one of the reaction processes at the predetermined intervals, estimates concentrations of a substance to be measured in the one of the specimens in the reaction vessel based on the parameters optimized by the parameter optimizing mechanism;

a determining mechanism which, when the actual values are measured for the one of the reaction processes at the predetermined intervals, determines whether or not a difference between a last one of the estimated concentrations of the substance and a previous one of the estimated concentrations of the substance falls within a predetermined range over time; and an output mechanism which outputs the last one of the concentrations of the substance to be measured when the determining mechanism determines that the difference falls within the predetermined range.

21. An automatic analyzer comprising:

a storage device which stores a plurality of approximate expressions each representing changes in a plurality of reaction processes of a plurality of specimens and reagents over time, each of the approximate expressions being associated with a corresponding test item or one of the specimens;

a photometer which measures one of the reaction processes of one of the specimens and reagents in a reaction vessel at predetermined intervals and outputs a plurality of actual values thereof; and a computer connected to the storage mechanism and the photometer to receive the actual values at predetermined intervals, and which is programmed to execute:

a parameter optimizing mechanism which, when the actual values are measured for the one of the reaction processes at the predetermined intervals, optimizes one or more parameters of one of the approximate expressions associated with the one of the specimens in the reaction vessel to fit the actual values of the one of the reaction processes measured by the photometer;

a measurement substance concentration calculating mechanism which, when the actual values are measured for the one of the reaction processes at the predetermined intervals, calculates concentrations of a measurement substance in the one of the specimens in the reaction vessel based on the parameters optimized by the parameter optimizing mechanism;

a determining mechanism which, when the actual values are measured for the one of the reaction processes at the predetermined intervals, determines whether or not a difference between a last one of the calculated concentrations of the measurement substance and a previous one of the calculated concentrations falls within a predetermined range over time; and a point-in-time storage mechanism to store a point in time at which the determining mechanism determines that the difference falls within the predetermined range.

22. The automatic analyzer according to claim 21, wherein:

the measurement substance concentration calculating mechanism calculates a concentration of an ordinary specimen based on the parameters optimized by the parameter optimizing mechanism at the point in time stored in the point-in-time storage mechanism.

* * * * *